United States Patent
Nagashima et al.

(10) Patent No.: US 10,363,551 B2
(45) Date of Patent: Jul. 30, 2019

(54) MONONUCLEAR IRON COMPLEX AND ORGANIC SYNTHESIS REACTION USING SAME

(71) Applicants: KYUSHU UNIVERSITY, NATIONAL UNIVERSITY CORPORATION, Fukuoka-shi, Fukuoka (JP); SHIN-ETSU CHEMICAL CO., LTD., Tokyo (JP)

(72) Inventors: Hideo Nagashima, Fukuoka (JP); Yusuke Sunada, Fukuoka (JP); Mina Sawano, Fukuoka (JP); Daisuke Noda, Fukuoka (JP); Koji Sakuta, Annaka (JP)

(73) Assignees: KYUSHU UNIVERSITY, NATIONAL UNIVERSITY CORPORATION, Fukuoka-Shi, Fukuoka (JP); SHIN-ETSU CHEMICAL CO., LTD., Tokyo (JP)

( * ) Notice: Subject to any disclaimer, the term of this patent is extended or adjusted under 35 U.S.C. 154(b) by 8 days.

(21) Appl. No.: 15/556,935

(22) PCT Filed: Mar. 8, 2016

(86) PCT No.: PCT/JP2016/057084
§ 371 (c)(1),
(2) Date: Sep. 8, 2017

(87) PCT Pub. No.: WO2016/143769
PCT Pub. Date: Sep. 15, 2016

(65) Prior Publication Data
US 2018/0243732 A1   Aug. 30, 2018

(30) Foreign Application Priority Data

Mar. 9, 2015 (JP) .................................. 2015-045797

(51) Int. Cl.
*C07C 5/03* (2006.01)
*B01J 31/16* (2006.01)
(Continued)

(52) U.S. Cl.
CPC .......... *B01J 31/1608* (2013.01); *B01J 31/22* (2013.01); *C07C 5/03* (2013.01); *C07C 9/15* (2013.01); *C07C 9/16* (2013.01); *C07C 13/10* (2013.01); *C07C 13/18* (2013.01); *C07C 13/465* (2013.01); *C07C 15/073* (2013.01); *C07C 15/18* (2013.01); *C07C 67/303* (2013.01); *C07C 69/24* (2013.01); *C07C 209/50* (2013.01); *C07C 211/04* (2013.01); *C07F 7/10* (2013.01); *C07F 7/1876* (2013.01); *C07F 15/02* (2013.01);
(Continued)

(58) Field of Classification Search
None
See application file for complete search history.

(56) References Cited

U.S. PATENT DOCUMENTS

2016/0023196 A1   1/2016   Nagashima et al.

FOREIGN PATENT DOCUMENTS

| JP | 2011-045798 A | 3/2011 |
| WO | WO 96/05207 A1 | 2/1996 |
| WO | WO 2014/133017 A1 | 9/2014 |

OTHER PUBLICATIONS

Gallego et al., Organometallics 2014, 33, 6885-6897. (Year: 2013).*

(Continued)

*Primary Examiner* — Clinton A Brooks
*Assistant Examiner* — Kofi Adzamli
(74) *Attorney, Agent, or Firm* — Birch, Stewart, Kolasch & Birch, LLP

(57) ABSTRACT

A mononuclear iron bivalent complex having iron-silicon bonds, which is represented by formula (1), can exhibit an excellent catalytic activity in at least one reaction selected from three reactions, i.e., a hydrosilylation reaction, a hydrogenation reaction and a reaction for reducing a carbonyl compound.

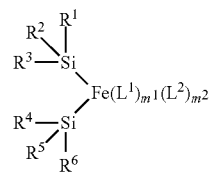

(1)

(In the formula, $R^1$ to $R^6$ independently represent a hydrogen atom, an alkyl group which may be substituted by X, or the like; X represents a halogen atom, or the like; $L^1$ represents at least one two-electron ligand selected from an isonitrile ligand, an amine ligand, an imine ligand, a nitrogenated heterocyclic ring, a phosphine ligand, a phosphite ligand and a sulfide ligand, wherein, when multiple $L^1$'s are present, two $L^1$'s may be bonded to each other; $L^2$ represents a two-electron ligand that is different from a CO ligand or the above-mentioned $L^1$, wherein, when multiple $L^2$'s are present, two $L^2$'s may be bonded to each other; and $m^1$ represents an integer of 1 to 4 and $m^2$ represents an integer of 0 to 3, wherein the sum total of $m^1$ and $m^2$ (i.e., $m^1+m^2$) satisfies 3 or 4.)

13 Claims, 3 Drawing Sheets

(51) Int. Cl.
  B01J 31/22      (2006.01)
  C07C 67/303    (2006.01)
  C07C 69/24     (2006.01)
  C07C 209/50    (2006.01)
  C07F 15/02     (2006.01)
  C07C 211/04    (2006.01)
  C07F 19/00     (2006.01)
  C07C 9/15      (2006.01)
  C07C 9/16      (2006.01)
  C07C 13/10     (2006.01)
  C07C 13/18     (2006.01)
  C07C 13/465    (2006.01)
  C07C 15/073    (2006.01)
  C07C 15/18     (2006.01)
  C07F 7/10      (2006.01)
  C07F 7/18      (2006.01)
  C07B 61/00     (2006.01)

(52) U.S. Cl.
  CPC ......... C07F 19/00 (2013.01); B01J 2231/323
      (2013.01); B01J 2531/842 (2013.01); C07B
      61/00 (2013.01); C07C 2531/22 (2013.01);
      C07C 2601/08 (2017.05); C07C 2601/14
      (2017.05); C07C 2602/08 (2017.05)

(56)           References Cited

OTHER PUBLICATIONS

Gallego et al., Organometallics, 2014, 33, p. 6885-6897. (Year: 2014).*
Bart et al., "Preparation and Molecular and Electronic Structures of Iron(0) Dinitrogen and Silane Complexes and Their Application to Catalytic Hydrogenation and Hydrosilation", Journal of the American Chemical Society, 2004, vol. 126, pp. 13794-13807.
Brown, "Reductions by Lithium Aluminum Hydride", Organic Reactions, 1941, vol. 6, pp. 469-493.
Carre et al., "Reactivity of μ-Silanediyl Iron Carbonyl Complexes with Alkynes. Molecular Structure of (CO)4FeSiPh2CEt=CEtSiPh2 and of (CO)3FeCMe=CMeSiPh2CMe=CMeFe(CO)3", Inorganic Chemistry, 1982, vol. 21, pp. 3099-3105.
Daida et al., "Considering FeII/IV Redox Processes as Mechanistically Relevant to the Catalytic Hydrogenation of Olefins by [PhBPiPr3]Fe—Hx Species", Inorganic Chemistry, 2004, vol. 43, pp. 7474-7485.
Das et al., "Two Iron Catalysts are Better than One: A General and Convenient Reduction of Aromatic and Aliphatic Primary Amides", Angewandte Chemie International Edition, 2012, vol. 51, pp. 1662-1666.
Frankel et al., "Homogeneous Hydrogenation of Methyl Linoleate Catalyzed by Iron Pentacarbonyl. Characterization of Methyl Octadecadienoate-Iron Tricarbonyl Complexes", Journal of Organic Chemistry, 1964, vol. 29, pp. 3292-3297.
Gallego et al., "Highly Electron-Rich Pincer-Type Iron Complexes Bearing Innocent Bis(metallylene)pyridine Ligands: Syntheses, Structures, and Catalytic Activity", Organometallics, 2014, vol. 33, pp. 6885-6897.
Harmon et al., "Hydrogenation of Organic Compounds Using Homogeneous Catalysts", Chemical Reviews, 1973, vol. 73, pp. 21-52.
Hudson et al., "Highly efficient iron(0) nanoparticle-catalyzed hydrogenation in water in flow", Green Chemistry, 2013, vol. 15, pp. 2141-2148.
Inagaki et al., "Asymmetric Iron-Catalyzed Hydrosilane Reduction of Ketones: Effect of Zinc Metal upon the Absolute Configuration", Angewandte Chemie International Edition, 2010, vol. 49, pp. 9384-9387.

Inagaki et al., "Iron- and Cobalt-Catalyzed Asymmetric Hydrosilylation of Ketones and Enones with Bis(oxazolinylphenyl)amine Ligands", Chemistry: A European Journal, 2010, vol. 16, pp. 3090-3096.
International Search Report for PCT/JP2016/057084 (PCT/ISA/210) dated May 24, 2016.
Kamata et al., "Catalytic Hydrosilylation of Alkenes by Iron Complexes Containing Terpyridine Derivatives as Ancillary Ligands", Organometallics, 2012, vol. 31, pp. 3825-3838.
Manna et al., "Salicylaldimine-Based Metal-Organic Framework Enabling Highly Active Olefin Hydrogenation with Iron and Cobalt Catalysts", Journal of the American Chemical Society, 2014, vol. 136, pp. 13182-13185.
Naumov et al., "Selective Dehydrogenative Silylation-Hydrogenation Reaction of Divinyldisiloxane with Hydrosilane Catalyzed by an Iron Complex", Journal of the American Chemical Society, 2012, vol. 134, pp. 804-807.
Nesmeyanov et al., "Addition, Substitution, and Telomerization Reactions of Olefins in the Presence of Metal Carbonyls or Colloidal Iron", Tetrahedron, 1962, vol. 17, p. 61-68.
Ohgushi et al., "Design and synthesis of novel disilaruthenacycle complexes and their application to catalytic reactions", The Chemical Society of Japan, 94th Spring Meeting Preprints, 2014, 2 pages, 2 PB-039.
Ohgushi et al., "Synthesis of novel disilaruthenacycle complexes and their applications in catalysis", The Society of Silicon Chemistry Japan, 18th Silicon Chemistry Association Symposium, 2014, 2 pages, P043.
Rangheard et al., "At the frontier between heterogeneous and homogeneous catalysis: hydrogenation of olefins and alkynes with soluble iron nanoparticles", Dalton Trans., 2010, vol. 39, pp. 8464-8471.
Schroeder et al., "Pentacarbonyliron(0) Photocatalyzed Hydrogenation and Isomerization of Olefins", Journal of the American Chemical Society, 1976, vol. 96, pp. 551-558.
Schroeder et al., "Pentacarbonyliron(0) Photocatalyzed Reactions of Trialkylsilanes with Alkenes", Journal of Organometallic Chemistry, 1977, vol. 128, pp. 345-358.
Schubert et al., "Transition-metal silyl complexes, 20. Investigations on the reactivity of the anionic silyl complexes [Fe(C0)3(PR3')SiR3]-", Chemische Berichte, 1987, vol. 120, pp. 1079-1085.
Silver, "Partial Mössbauer quadrupole splittings in low-spin iron(II) compounds: properties of bidentate phosphine ligands and possibilities to forecast when complexes can be prepared for octahedral low-spin iron(II)", Inorganica Chimica Acta, 1991, vol. 184, pp. 235-242.
Sunada et al., "Disilaferracycle Dicarbonyl Complex Containing Weakly Coordinated η2-(H—Si) Ligands: Application to C—H Functionalization of Indoles and Arenes", Organometallics, 2014, vol. 33, pp. 5936-5939.
Sunada et al., "Hydrosilane Reduction of Tertiary Carboxamides by Iron Carbonyl Catalysts", Angewandte Chemie International Edition, 2009, vol. 48, pp. 9511-9514.
Sunada et al., "Synthesis and reactions of ruthenium complexes bearing a disilametallacycle skeleton", The Kinki Chemical Society, 61st Organometallic Chemistry Symposium Preprints, 2014, 2 pages, P2B-13.
Tondreau et al., "Iron Catalysts for Selective Anti-Markovnikov Alkene Hydrosilylation Using Tertiary Silanes", Science, 2012, vol. 335, pp. 567-570.
Tsutsumi et al., "New catalyst systems for iron-catalyzed hydrosilane reduction of carboxamides", Chemical Communications, 2011, vol. 47, pp. 6581-6583.
Written Opinion of the International Searching Authority for PCT/JP2016/057084 (PCT/ISA/237) dated May 24, 2016.
Yu et al., "High-Activity Iron Catalysts for the Hydrogenation of Hindered, Unfunctionalized Alkenes", ACS Catalysis, 2012, vol. 2, pp. 1760-1764.
Zhou et al., "A Convenient and General Iron-Catalyzed Reduction of Amides to Amines", Angewandte Chemie International Edition, 2009, vol. 48, pp. 9507-9510.
Extended European Search Report dated Sep. 11, 2018 in European Patent Application No. 16761737.2.

(56) References Cited

OTHER PUBLICATIONS

Zhang, H, et al. "(Aminocarbene)(Divinyltetramethyldisiloxane)Iron(0) Compounds: A Class of Low-Coordinate Iron(0) Reagents" Angewandte Chemie, International Edition, vol. 53, No. 32, Jun. 24, 2014, pp. 8432-8436, XP002784002.

* cited by examiner

MONONUCLEAR IRON COMPLEX AND ORGANIC SYNTHESIS REACTION USING SAME

TECHNICAL FIELD

This invention relates to a mononuclear iron complex having iron-silicon bonds, and more particularly, to a mononuclear iron complex having catalytic activity to at least one reaction selected from among industrially useful hydrosilylation reaction, hydrogenation reaction, and reductive reaction of carbonyl compounds.

BACKGROUND ART

Hydrosilylation reaction involving addition reaction of a Si—H functionality compound to a compound having a carbon-carbon double or triple bond is a useful means for synthesizing organosilicon compounds and is also industrially important synthetic reaction.

Pt, Pd and Rh compounds are known as catalysts for the hydrosilylation reaction. Most often used among them are Pt compounds as typified by Speier catalysts and Karstedt catalysts.

One of problems associated with Pt compound-catalyzed reactions is that the addition of a Si—H functionality compound to terminal olefin entails side reaction or internal rearrangement of olefin. Since this system does not display addition reactivity to internal olefin, unreacted olefin is left in the addition product. To complete the reaction, the olefin must be used previously in excess by taking into account the portion that is left behind due to side reaction.

Another problem is low selectivity between $\alpha$- and $\beta$-adducts depending on the identity of olefin.

The most serious problem is that all Pt, Pd and Rh as the center metal are very expensive noble metal elements. Since metal compound catalysts which can be used at lower cost are desired, a number of research works have been made thereon.

For example, reaction in the presence of iron-carbonyl complexes such as $Fe(CO)_5$ and $Fe_3(CO)_{12}$ is known from Non-Patent Document 1. For this reaction, reaction conditions including a high temperature of 160° C., or light irradiation is necessary (Non-Patent Document 2).

Non-Patent Document 3 reports exemplary reaction of methylvinyldisiloxane with methylhydrogendisiloxane using an iron-carbonyl complex having a cyclopentadienyl group as ligand. In this reaction, dehydrogenation silylation reaction takes place preferentially.

Non-Patent Document 4 describes reaction using an iron catalyst having a pyridine ligand. A large excess of reducing agent ($NaBHEt_3$) is necessary as reaction aid. Although $PhSiH_3$ and $Ph_2SiH_2$ add to olefins, more useful trialkylsilanes, alkoxysilanes and siloxanes have poor addition reactivity to olefins.

Non-Patent Documents 5 and 6 report Fe complexes having a bisiminopyridine ligand. It is disclosed that they display good reactivity to alkoxysilanes and siloxanes under mild conditions. The reaction using these complexes, however, has several problems including low reactivity to internal olefin, use of sodium amalgam, which consists of water-prohibitive sodium and highly toxic mercury and requires careful handling, or use of water-prohibitive $NaBEt_3H$ during the synthesis of the complex, and low stability of the complex compound itself, which requires handling in a special equipment like glovebox and storage in nitrogen atmosphere.

On the other hand, a number of reports are made on hydrogenation reaction of olefins. For example, Non-Patent Document 7 reports hydrogenation by thermal reaction using $Fe(CO)_5$ catalyst, and Non-Patent Document 8 reports hydrogenation by photo-reaction. However, the thermal reaction requires high-temperature (180° C.) and high-pressure (28 atm.) conditions, and the turnover number is as low as 0.5. It is not concluded that the catalyst has sufficient activity. Also the photo-reaction can take place even at room temperature, but a turnover number of 33 is still insufficient.

Non-Patent Document 9 reports exemplary iron-catalyzed reaction using an organoaluminum compound as a cocatalyst. A turnover number of 17 indicates low catalytic activity.

Non-Patent Document 10 reports exemplary reaction using an iron chloride catalyst in combination with a Grignard reagent as a cocatalyst. The system allows reaction to run at room temperature, but requires high-pressure (20 atm.) conditions, and the turnover number is as low as 20.

Non-Patent Document 11 reports an iron catalyst having a phosphorus ligand. Although the system allows reaction to run at room temperature and a relatively low pressure (4 atm.), the reactants are limited to styrene and some alkenes, and the turnover number is not regarded sufficient.

Also, Non-Patent Document 5 cited above reports an exemplary iron catalyst having a bisiminopyridine ligand. Reactivity is satisfactory as demonstrated by a turnover number of 1,814 at room temperature and a relatively low pressure (4 atm.). This reaction suffers from problems including safety upon synthesis and stability of the relevant compound like the aforementioned iron complex having a bisiminopyridine ligand.

Also, Non-Patent Document 12 discloses an iron catalyst supported on a polymer. Despite the advantage of possible repetitive reuse, the applicable range is limited because the use of water as the solvent is essential.

Non-Patent Document 13 discloses an iron catalyst supported on a metal-organic framework (MOF). Despite the advantage of possible repetitive reuse, the catalyst precursor must be activated with strong reducing agents.

There are reported no examples where these prior art catalysts are applied to hydrogenation reaction of tri- or tetra-substituted olefins which is generally believed difficult.

Non-Patent Document 14 discloses a mononuclear iron complex which is effective for hydrogenation reaction of tetra-substituted olefins which is generally believed difficult. A long reaction time of 48 hours is necessary and the turnover number is as small as 20.

One known method for reducing carbonyl compounds is by using hydride reagents such as aluminum hydride and boron hydride or hydrogenation in the presence of noble metal catalysts. For ketones and aldehydes among carbonyl compounds, there are known hydride reagents and hydrogenation catalysts containing noble metals which allow progress of reaction under mild conditions and are stable and easy to handle. For reducing carboxylic acid derivatives such as esters and amides, the main method uses strong reducing agents such as lithium aluminum hydride and borane (Non-Patent Document 15). However, since these reducing agents are flammable, water-sensitive substances, they are awkward to handle. Also careful operation is necessary when the aluminum or boron compound is removed from the desired compound after the reaction. In addition, high pressure of hydrogen and high reaction temperature are necessary for the reduction of carboxylic acid derivatives.

There are reported many methods using methylhydrogenpolysiloxane and hydrosilane compounds which are stable in air and easy to handle, as the reducing agent. For this reaction, however, addition of strong acids or Lewis acids is necessary as well as expensive noble metal catalysts. One recent report relates to reductive reaction of carbonyl compounds in the presence of inexpensive iron catalysts. In some examples, the catalyst is applied to reductive reaction of amides that requires rigorous conditions in the prior art. While illustrative examples of the iron catalyst are given in Non-Patent Documents 16 to 21, there is a desire to have high activity catalysts displaying a greater turnover number.

Also, Non-Patent Documents 22 to 24 report mononuclear ruthenium complexes as the metal complex compound having catalytic activity to hydrosilylation reaction, hydrogenation reaction, or reductive reaction of carbonyl compounds. On use of these ruthenium complexes, any of the reactions runs under relatively mild conditions. Yet catalysts using less expensive metals are desired as mentioned above.

PRIOR ART DOCUMENTS

Non-Patent Documents

Non-Patent Document 1: A. N. Nesmeyanov, et al., Tetrahedron, 1962, 17, 61
Non-Patent Document 2: M. S. Wrighton, et al., J. Organomet. Chem., 1977, 128, 345
Non-Patent Document 3: H. Nakazawa, et al., J. Am. Chem. Soc., 2012, 134, 804
Non-Patent Document 4: H. Nakazawa, et al., Organometallics, 2012, 31, 3825
Non-Patent Document 5: P. J. Chirik, et al., J. Am. Chem. Soc., 2004, 126, 13794
Non-Patent Document 6: P. J. Chirik, et al., Science, 2012, 335, 567
Non-Patent Document 7: Frankel, et al., J. Org. Chem., 1964, 29, 3292
Non-Patent Document 8: M. S. Wrighton, et al., J. Am. Chem. Soc., 1976, 98, 551
Non-Patent Document 9: R. E. Harmon, et al., J. Chem. Rev., 1973, 73, 21
Non-Patent Document 10: L. Lefort, et al., Dalton Trans., 2010, 39, 8464
Non-Patent Document 11: J. C. Peters, et al., Inorg. Chem., 2004, 43, 7474
Non-Patent Document 12: R. Hudson, et al., Green Chem, 2013, 15, 2141
Non-Patent Document 13: K. Manna, et al., J. Am. Chem. Soc., 2014, 136, 13182
Non-Patent Document 14: P. J. Chirik, et al., Acs. Catal., 2012, 2, 1760
Non-Patent Document 15: W. R. Brown, Organic Reactions, 1941, 6, 470
Non-Patent Document 16: H. Nagashima, et al., Angew. Chem. Int. Ed., 2009, 48, 9511
Non-Patent Document 17: M. Beller, et al., Angew. Chem. Int. Ed., 2009, 48, 9507
Non-Patent Document 18: H. Nishiyama, et al., Angew. Chem. Int. Ed., 2010, 49, 9384
Non-Patent Document 19: H. Nishiyama, et al., Chem. Eur. J., 2010, 16, 3090
Non-Patent Document 20: H. Nagashima, et al., Chem. Commun., 2011, 47, 6581
Non-Patent Document 21: M. Beller, et al., Angew. Chem., 2012, 51, 1662
Non-Patent Document 22: Ohgushi, Sunada & Nagashima, Development and catalytic action of novel ruthenium complexes bearing disilametallacycle skeleton, Japan Chemical Society, 94-th Spring Meeting Preprints, 2014, 2PB-039
Non-Patent Document 23: Sunada, Inoue, Ohgushi & Nagashima, Development and catalytic function of novel ruthenium complexes bearing disilametallacycle skeleton, 61-st Organometallic Chemistry Symposium Preprints, 2014, 2PB-13
Non-Patent Document 24: Ohgushi, Yamamoto, Sunada & Nagashima, Development and catalytic action of novel ruthenium complexes bearing disilametallacycle skeleton, 18-th Silicon Chemistry Association Symposium, 2014, P43

SUMMARY OF THE INVENTION

Problems to be Solved by the Invention

An object of the invention, which has been made under the above circumstances, is to provide a mononuclear iron complex having iron-silicon bonds that displays high catalytic activity to at least one of three reactions: hydrosilylation reaction, hydrogenation reaction, and reductive reaction of carbonyl compounds, and a method for carrying out each of the reactions under mild conditions in the presence of the complex.

Means for Solving the Problems

Making extensive investigations to solve the outstanding problems, the inventors have found that a specific mononuclear iron bivalent complex having iron-silicon bonds displays high catalytic activity to at least one of hydrosilylation reaction, hydrogenation reaction, and reductive reaction of carbonyl compounds, and allows the reaction to run under mild conditions. The invention is completed based on this finding.

Namely, the present invention provides the following.

1. A mononuclear iron bivalent complex having formula (1):

[Chemical Formula 1]

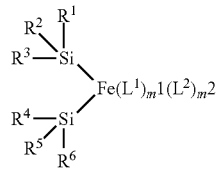

(1)

wherein $R^1$ to $R^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl or organothio group which may be substituted with X, or at least one pair of any one of $R^1$ to $R^3$ and any one of $R^4$ to $R^6$, taken together, represent a crosslinking substituent, X is a halogen atom, organoxy, monoorganoamino, diorganoamino or organothio group, $L^1$ is at least one two-electron ligand selected from the group consisting of isonitrile, amine, imine, nitrogen-containing heterocyclic ring, phosphine, phosphite, and sulfide, with the proviso that when a plurality of $L^1$'s are present, two $L^1$'s may bond together, $L^2$ is a two-electron ligand other than CO ligand and $L^1$, with the proviso that when a plurality of $L^2$'s are present, two $L^2$'s may bond together, $m^1$ is an integer of 1 to 4, $m^2$ is an integer of 0 to 3, and $m^1+m^2$ is 3 or 4.

2. The mononuclear iron bivalent complex of 1 wherein $L^1$ is isonitrile, with the proviso that when a plurality of $L^1$'s are present, two $L^1$'s may bond together.

3. The mononuclear iron bivalent complex of 1 or 2 wherein $L^2$ is triorganohydrosilane, with the proviso that when a plurality of $L^2$'s are present, two $L^2$'s may bond together.

4. The mononuclear iron bivalent complex of any one of 1 to 3 wherein $m^1$ and $m^2$ each are 2.

5. The mononuclear iron bivalent complex of 4 wherein $R^1$ to $R^6$ are each independently an alkyl, aryl or aralkyl group which may be substituted with X which is as defined above, $L^2$ is a triorganohydrosilane represented by H—$SiR^7R^8R^9$ or H—$SiR^{10}R^{11}R^{12}$ wherein $R^7$ to $R^{12}$ are each independently an alkyl, aryl or aralkyl group which may be substituted with X which is as defined above, at least one pair of any one of $R^1$ to $R^3$ and any one of $R^4$ to $R^6$ or any one of $R^7$ to $R^9$, or at least one pair of any one of $R^{10}$ to $R^{12}$ and any one of $R^4$ to $R^6$ or any one of $R^7$ to $R^9$ may bond together to form a crosslinking substituent, or at least one pair of any one of $R^1$ to $R^3$ and any one of $R^4$ to $R^6$ or any one of $R^7$ to $R^9$ may bond together to form a crosslinking substituent, and at least one pair of any one of $R^{10}$ to $R^{12}$ and any one of $R^4$ to $R^6$ or any one of $R^7$ to $R^9$ may bond together to form a crosslinking substituent.

6. The mononuclear iron bivalent complex of any one of 1 to 5 wherein any one of $R^1$ to $R^3$ and any one of $R^4$ to $R^6$ bond together to form a crosslinking substituent.

7. The mononuclear iron bivalent complex of 5 wherein any one of $R^1$ to $R^3$ and any one of $R^4$ to $R^6$ or any one of $R^7$ to $R^9$ bond together to form a crosslinking substituent, and any one of $R^{10}$ to $R^{12}$ and a substituent on Si which is selected from any one of $R^4$ to $R^6$ and any one of $R^7$ to $R^9$ and which does not participate in formation of said crosslinking substituent bond together to form a crosslinking substituent.

8. The mononuclear iron bivalent complex of 7 wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and any one of $R^{10}$ to $R^{12}$ and any one of $R^7$ to $R^9$ bond together to form an o-phenylene group which may be substituted with Y which is as defined above.

9. A catalyst comprising the mononuclear iron bivalent complex of any one of 1 to 8, the catalyst having activity to at least one reaction selected from hydrosilylation reaction, hydrogenation reaction, and reductive reaction of carbonyl compounds.

10. A method for preparing an addition compound, comprising the step of effecting hydrosilylation reaction of a compound having an aliphatic unsaturated bond with a hydrosilane or organohydropolysiloxane having a Si—H bond in the presence of the catalyst of 9.

11. A method for preparing an alkane compound, comprising the step of hydrogenating a compound having an aliphatic unsaturated bond in the presence of the catalyst of 9.

12. A method for preparing an amine compound, comprising the step of reducing an amide compound with a silane or organohydropolysiloxane having a Si—H bond in the presence of the catalyst of 9.

13. A method for preparing an alcohol compound, comprising the step of reducing an aldehyde, ketone or ester compound with a silane or organohydropolysiloxane having a Si—H bond in the presence of the catalyst of 9.

Advantageous Effects of the Invention

When hydrosilylation reaction of an aliphatic unsaturated group-containing compound with a silane or polysiloxane having a Si—H group is carried out using a mononuclear iron complex of the invention as the catalyst, addition reaction can occur under conditions from room temperature to 100° C. In particular, addition reaction with industrially useful polysiloxanes, and trialkoxysilanes and dialkoxysilanes takes place in an effective manner. Although many of the known documents indicate that in the relevant reaction, dehydrogenation silylation reaction to form unsaturated group-containing compounds takes place preferentially to addition reaction to unsaturated group, the use of the inventive catalyst ensures preferential progress of addition reaction to unsaturated group.

Hydrogenation reaction is possible under mild conditions including room temperature to 100° C. and a hydrogen gas atmosphere of about 1 to 20 atm. The catalyst is also effective for hydrogenation of multi-substituted alkenes which is difficult with prior art methods.

In reductive reaction of carbonyl compounds, amide, aldehyde, ketone and ester compounds may be reacted with silanes or polysiloxanes having a Si—H group which are easy to handle, thereby yielding the desired reduced compounds.

EMBODIMENT FOR CARRYING OUT THE INVENTION

Figure 1:
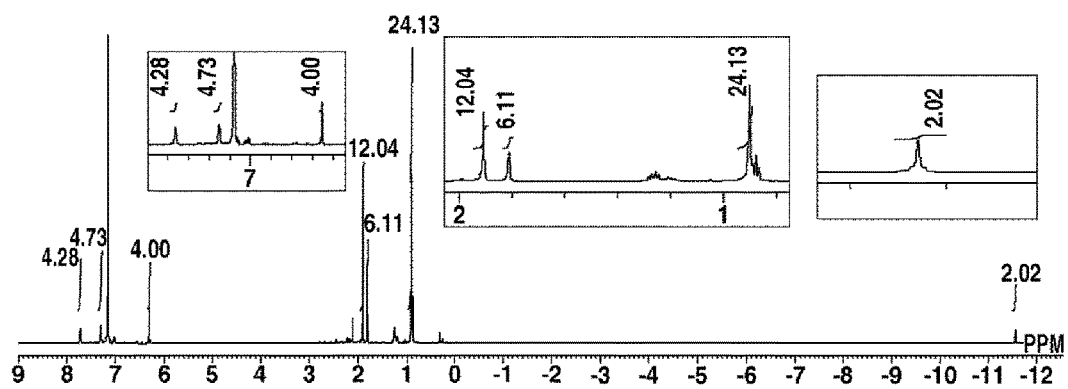
FIG. 1 is a diagram showing $^1$H-NMR spectrum of iron complex A in Example 1.

Now the invention is described in detail.

The mononuclear iron complex of the invention is a bivalent complex having two Fe—Si bonds and having two-electron ligands ($L^1$, $L^2$) other than carbon monoxide (CO) coordinated to Fe, at least one $L^1$ being included and the total of $L^1$ and $L^2$ being three or four, as represented by formula (1).

[Chemical Formula 2]

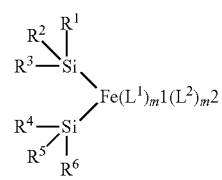

(1)

In formula (1), $R^1$ to $R^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl or organothio group which may be substituted with X, or at least one pair of any one of $R^1$ to $R^3$ and any one of $R^4$ to $R^6$, taken together, represent a crosslinking substituent, and X is a halogen atom, an organoxy, monoorganoamino, diorganoamino or organothio group.

The alkyl group may be straight, branched or cyclic. Although its carbon count is not particularly limited, alkyl groups of 1 to 30 carbons, more preferably 1 to 10 carbons are preferable. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, and cyclononyl.

For the aryl group, aryl groups of 6 to 30 carbons, more preferably 6 to 20 carbons are preferable although the carbon count is not particularly limited. Examples include phenyl, 1-naphthyl, 2-naphthyl, anthryl, phenanthryl, o-biphenylyl, m-biphenylyl, and p-biphenylyl.

For the aralkyl group, aralkyl groups of 7 to 30 carbons, more preferably 7 to 20 carbons are preferable although the carbon count is not particularly limited. Examples include benzyl, phenylethyl, phenylpropyl, naphthylmethyl, naphthylethyl, and naphthylpropyl.

Suitable organooxy groups include, but are not limited to, alkoxy, aryloxy and aralkyloxy groups represented by RO wherein R is a substituted or unsubstituted $C_1$-$C_{30}$ alkyl group, $C_6$-$C_{30}$ aryl group or $C_7$-$C_{30}$ aralkyl group.

Suitable alkoxy group include, but are not limited to, alkoxy groups of 1 to 30 carbons, more preferably 1 to 10 carbons are preferable. Examples include methoxy, ethoxy, n-propoxy, i-propoxy, c-propoxy, n-butoxy, i-butoxy, s-butoxy, t-butoxy, n-pentoxy, n-hexoxy, n-heptyloxy, n-octyloxy, n-nonyloxy, and n-decyloxy.

Suitable aryloxy groups include, but are not limited to, aryloxy groups of 6 to 30 carbons, more preferably 6 to 20 carbons. Examples include phenoxy, 1-naphthyloxy, 2-naphthyloxy, anthryloxy, and phenanthryloxy.

Suitable aralkyloxy groups include, but are not limited to, aralkyloxy groups of 7 to 30 carbons, more preferably 7 to 20 carbons. Examples include benzyloxy, phenylethyloxy, phenylpropyloxy, 1 or 2-naphthylmethyloxy, 1 or 2-naphthylethyloxy, 1 or 2-naphthylpropyloxy.

Suitable organothio groups include the foregoing organooxy groups whose oxygen atom is replaced by sulfur atom.

The monoorganoamino group is preferably a group of $RNH_2$ wherein R is as defined above, though not limited thereto. The preferred carbon count of R is the same as defined above for the alkoxy, aryloxy and aralkyloxy groups. Examples include straight or branched monoalkylamino groups such as methylamino, ethylamino, n-propylamino, isopropylamino, n-butylamino, isobutylamino, s-butylamino, t-butylamino, n-pentylamino, n-hexylamino, n-heptylamino, n-octylamino, n-nonylamino, n-decylamino, n-undecylamino, n-dodecylamino, n-tridecylamino, n-tetradeylamino, n-pentadecylamino, n-hexadecylamino, n-heptadecylamino, n-octadecylamino, n-nonadecylamino, and n-eicosanylamino; monocycloalkylamino groups such as cyclopropylamino, cyclobutylamino, cyclopentylamino, cyclohexylamino, cycloheptylamino, cyclooctylamino, and cyclononylamino; monoarylamino groups such as anilino, 1 or 2-naphthylamino; and monoaralkylamino groups such as benzylamino, phenylethylamino, phenylpropylamino, 1 or 2-naphthylmethylamino.

The diorganoamino group is preferably a group of $R_2NH$ wherein R is independently as defined above, though not limited thereto. The preferred carbon count of R is the same as defined above for the alkoxy, aryloxy and aralkyloxy groups. Examples include straight or branched dialkylamino groups such as dimethylamino, diethylamino, di-n-propylamino, diisopropylamino, di-n-butylamino, diisobutylamino, di-s-butylamino, di-t-butylamino, di-n-pentylamino, di-n-hexylamino, di-n-heptylamino, di-n-octylamino, di-n-nonylamino, di-n-decylamino, di-n-undecylamino, di-n-dodecylamino, di-n-tridecylamino, di-n-tetradeylamino, di-n-pentadecylamino, di-n-hexadecylamino, di-n-heptadecylamino, di-n-octadecylamino, di-n-nonadecylamino, di-n-eicosanylamino, N-ethylmethylamino, N-isopropylmethylamino, and N-butylmethylamino; dicycloalkylamino groups such as dicyclopropylamino, dicyclobutylamino, dicyclopentylamino, dicyclohexylamino, dicycloheptylamino, dicyclooctylamino, dicyclononylamino, and cyclopentylcyclohexylamino; alkylarylamino groups such as N-methylanilino, N-ethylanilino, and N-n-propylanilino; diarylamino groups such as diphenylamino, 4,4'-bisnaphthylamino, N-phenyl-1 or 2-naphthylamino; and diaralkylamino groups such as dibenzylamino, bis(phenylethyl)amino, bis(phenylpropyl)amino, bis(1 or 2-naphthylmethyl)amino.

The monoorganophosphino group is preferably a group of RPH wherein R is as defined above, though not limited thereto. The preferred carbon count of R is the same as defined above for the alkoxy, aryloxy and aralkyloxy groups. Examples include straight or branched monoalkylphosphino groups such as methylphosphino, ethylphosphino, n-propylphosphino, isopropylphosphino, n-butylphosphino, isobutylphosphino, s-butylphosphino, t-butylphosphino, n-pentylphosphino, n-hexylphosphino, n-heptylphosphino, n-octylphosphino, n-nonylphosphino, n-decylphosphino, n-undecylphosphino, n-dodecylphosphino, n-tridecylphosphino, n-tetradeylphosphino, n-pentadecylphosphino, n-hexadecylphosphino, n-heptadecylphosphino, n-octadecylphosphino, n-nonadecylphosphino, and n-eicosanylphosphino; monocycloalkylphosphino groups such as cyclopropylphosphino, cyclobutylphosphino, cyclopentylphosphino, cyclohexylphosphino, cycloheptylphosphino, cyclooctylphosphino, and cyclononylphosphino; monoarylphosphino groups such as phenylphosphino, 1 or 2-naphthylphosphino; and monoaralkylphosphino groups such as benzylphosphino.

The diorganophosphino group is preferably a group of $R_2P$ wherein R is independently as defined above, though not limited thereto. The preferred carbon count of R is the same as defined above for the alkoxy, aryloxy and aralkyloxy groups.

Examples include straight or branched dialkylphosphino groups such as dimethylphosphino, diethylphosphino, di-n-propylphosphino, diisopropylphosphino, di-n-butylphosphino, diisobutylphosphino, di-s-butylphosphino, di-t-butylphosphino, di-n-pentylphosphino, di-n-hexylphosphino, di-n-heptylphosphino, di-n-octylphosphino, di-n-nonylphosphino, di-n-decylphosphino, di-n-undecylphosphino, di-n-dodecylphosphino, di-n-tridecylphosphino, di-n-tetradeylphosphino, di-n-pentadecylphosphino, di-n-hexadecylphosphino, di-n-heptadecylphosphino, di-n-octadecylphosphino, di-n-nonadecylphosphino, and di-n-eicosanylphosphino; dicycloalkylphosphino groups such as dicyclopropylphosphino, dicyclobutylphosphino, dicyclopentylphosphino, dicyclohexylphosphino, dicycloheptylphosphino, dicyclooctylphosphino, and dicyclononylphosphino; alkylarylphosphino groups such as cyclohexylphenylphosphino; diarylphosphino groups such as diphenylphosphino, bis(1 or 2-naphthyl)phosphino; and diaralkylphosphino groups such as dibenzylphosphino, bis(phenylethyl)phosphino, bis(1 or 2-naphthylmethyl)phosphino.

The monoorganosilyl group is preferably a group of $RSiH_2$ wherein R is as defined above, though not limited thereto. The preferred carbon count of R is the same as defined above for the alkoxy, aryloxy and aralkyloxy groups. Examples include straight or branched monoalkylsilyl groups such as methylsilyl, ethylsilyl, n-propylsilyl, isopropylsilyl, n-butylsilyl, isobutylsilyl, s-butylsilyl, t-butylsilyl, n-pentylsilyl, n-hexylsilyl, n-heptylsilyl, n-octylsilyl, n-nonylsilyl, n-decylsilyl, n-undecylsilyl, n-dodecylsilyl, n-tridecylsilyl, n-tetradecylsilyl, n-pentadecylsilyl, n-hexadecylsilyl, n-heptadecylsilyl, n-octadecylsilyl, n-nonadecylsilyl, and n-eicosanylsilyl; monocycloalkylsilyl groups such as cyclopropylsilyl, cyclobutylsilyl, cyclopentylsilyl, cyclohexylsilyl, cycloheptylsilyl, cyclooctylsilyl, and cyclononylsilyl; monoarylsilyl groups such as phenylsilyl, 1 or 2-naphthylsilyl; and monoaralkylsilyl groups such as benzylsilyl, phenylethylsilyl, phenylpropylsilyl, 1 or 2-naphthylmethylsilyl.

The diorganosilyl group is preferably a group of $R_2SiH$ wherein R is independently as defined above, though not limited thereto. The preferred carbon count of R is the same as defined above for the alkoxy, aryloxy and aralkyloxy groups. Examples include straight or branched dialkylsilyl groups such as dimethylsilyl, diethylsilyl, di-n-propylsilyl, diisopropylsilyl, di-n-butylsilyl, diisobutylsilyl, di-s-butylsilyl, di-t-butylsilyl, di-n-pentylsilyl, di-n-hexylsilyl, di-n-heptylsilyl, di-n-octylsilyl, di-n-nonylsilyl, di-n-decylsilyl, di-n-undecylsilyl, di-n-dodecylsilyl, di-n-tridecylsilyl, di-n-tetradeylsilyl, di-n-pentadecylsilyl, di-n-hexadecylsilyl, di-n-heptadecylsilyl, di-n-octadecylsilyl, di-n-nonadecylsilyl, di-n-eicosanylsilyl, ethylmethylsilyl, isopropylmethylsilyl, and butylmethylsilyl; dicycloalkylsilyl groups such as dicyclopropylsilyl, dicyclobutylsilyl, dicyclopentylsilyl, dicyclohexylsilyl, dicycloheptylsilyl, dicyclooctylsilyl, dicyclononylsilyl, and cyclopentylcyclohexylsilyl; alkylarylsilyl groups such as methylphenylsilyl, ethylphenylsilyl, and n-propylphenylsilyl; diarylsilyl groups such as diphenylsilyl, bis(1 or 2-naphthyl)silyl, phenyl-1 or 2-naphthylsilyl; and diaralkylsilyl groups such as dibenzylsilyl, bis(phenylethyl)silyl, bis(phenylpropyl)silyl, and bis(1 or 2-naphthylmethyl)silyl.

The triorganosilyl group is preferably a group of $R_3Si$ wherein R is independently as defined above, though not limited thereto. The preferred carbon count of R is the same as defined above for the alkoxy, aryloxy and aralkyloxy groups. Examples include straight or branched trialkylsilyl groups such as trimethylsilyl, triethylsilyl, tri-n-propylsilyl, triisopropylsilyl, tri-n-butylsilyl, triisobutylsilyl, tri-s-butylsilyl, tri-t-butylsilyl, tri-n-pentylsilyl, tri-n-hexylsilyl, tri-n-heptylsilyl, tri-n-octylsilyl, tri-n-nonylsilyl, tri-n-decylsilyl, tri-n-undecylsilyl, tri-n-dodecylsilyl, tri-n-tridecylsilyl, tri-n-tetradeylsilyl, tri-n-pentadecylsilyl, tri-n-hexadecylsilyl, tri-n-heptadecylsilyl, tri-n-octadecylsilyl, tri-n-nonadecylsilyl, tri-n-eicosanylsilyl, ethyldimethylsilyl, diisopropylmethylsilyl, and dibutylmethylsilyl; tricycloalkylsilyl groups such as tricyclopropylsilyl, tricyclobutylsilyl, tricyclopentylsilyl, tricyclohexylsilyl, tricycloheptylsilyl, tricyclooctylsilyl, and tricyclononylsilyl; alkylarylsilyl groups such as methyldiphenylsilyl, ethyldiphenylsilyl, and n-propyldiphenylsilyl; triarylsilyl groups such as triphenylsilyl, tri(1 or 2-naphthyl)silyl, diphenyl-1 or 2-naphthylsilyl; and triaralkylsilyl groups such as tribenzylsilyl, tri(phenylethyl)silyl, tri(phenylpropyl)silyl, tri(1 or 2-naphthylmethyl)silyl.

With respect to the foregoing substituent groups, at least one hydrogen atom on R may be substituted by a substituent X. Suitable substituents X include halogen, organoxy, monoorganoamino, diorganoamino, and organothio groups, and examples of the organoxy, monoorganoamino, diorganoamino, and organothio groups are as exemplified above.

Exemplary of the halogen are fluorine, chlorine, bromine and iodine, with fluorine being preferred. Suitable fluorine-substituted alkyl groups include trifluoropropyl, nonafluorohexyl and heptadecylfluorodecyl.

Of the foregoing substituent groups, $R^1$ to $R^6$ are each independently selected preferably from $C_1$-$C_{30}$ alkyl, $C_6$-$C_{30}$ aryl, and $C_7$-$C_{30}$ aralkyl groups which may be substituted with X, more preferably from $C_1$-$C_{10}$ alkyl and $C_6$-$C_{10}$ aryl groups.

When a pair of any one of $R^1$ to $R^3$ and any one of $R^4$ to $R^6$, taken together, represent a crosslinking substituent, the crosslinking substituent is not particularly limited as long as it is capable of crosslinking two silicon atoms. Exemplary crosslinking substituents include —O—, —S—, —NH—, —NR— wherein R is as defined above, —PR— wherein R is as defined above, —NH—$(CH_2)_k$—NH— wherein k is an integer of 1 to 10, —NR—$(CH_2)_k$—NR— wherein k is as defined above and R is independently as defined above, —PH—$(CH_2)_k$—PH— wherein k is as defined above, —PR—$(CH_2)_k$—PR— wherein k is as defined above and R is independently as defined above, —C≡C—, $C_1$-$C_{10}$ alkylene, $C_6$-$C_{30}$ arylene, $C_7$-$C_{30}$ aralkylene, —$(CH_2O)_k$— wherein k is as defined above, —$(CH_2)_k$—O—$(CH_2)_k$— wherein k is independently as defined above, —O—$(CH_2)_k$—O— wherein k is as defined above, —R'—O—$(CH_2)_k$—O—R'— wherein R' is each independently a $C_1$-$C_{10}$ alkylene group, $C_6$-$C_{30}$ arylene group or $C_7$-$C_{30}$ aralkylene group and k is as defined above, —$(CH_2S)_k$— wherein k is as defined above, —$(CH_2)_k$—S—$(CH_2)_k$— wherein k is independently as defined above, —S—$(CH_2)_k$—S— wherein k is as defined above, —R'—S—$(CH_2)_k$—O—R'— wherein R' is independently as defined above and k is as defined above, —$SiR_2$— wherein R is independently as defined above, and —$(CH_2)_k$—$SiR_2$—$(CH_2)_k$— wherein R is independently as defined above and k is independently as defined above.

Suitable $C_1$-$C_{10}$ alkylene groups include methylene, ethylene, propylene, trimethylene, tetramethylene, pentamethylene, and hexamethylene.

Suitable $C_6$-$C_{30}$ arylene groups include o-phenylene (1,2-phenylene), 1,2-naphthylene, 1,8-naphthylene, and 2,3-naphthylene.

Suitable $C_7$-$C_{30}$ aralkylene groups include —$(CH_2)_k$—Ar— wherein Ar is a $C_6$-$C_{20}$ arylene group and k is as defined above, —Ar—$(CH_2)_k$— wherein Ar and k are as defined above, and —$(CH_2)_k$—Ar—$(CH_2)_k$— wherein Ar is as defined above and k is independently as defined above.

Notably, in the foregoing alkylene, arylene and aralkylene groups, at least one hydrogen atom may be substituted by a substituent X wherein X is as defined above.

Assume that Z stands for a crosslinking substituent. Since the number of Z linking two silicon atoms is 1 to 3, the mononuclear iron complex having a crosslinking substituent Z is represented by the following formulae.

[Chemical Formula 3]

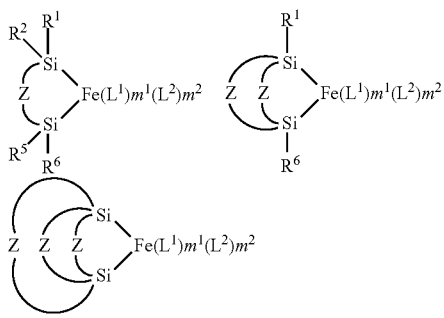

Herein $R^1$, $R^2$, $R^5$, $R^6$, $L^1$, $L^2$, $m^1$ and $m^2$ are as defined above, and Z is a crosslinking substituent.

Illustrative examples of the disilametallacycle structure having a crosslinking substituent include those of the following formulae, but are not limited thereto.

[Chemical Formula 4]

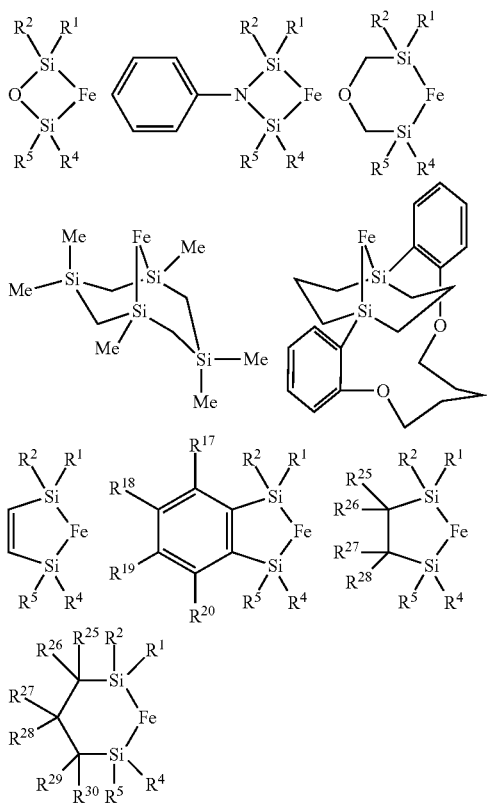

Herein Me stands for methyl.

In the above formulae, $R^1$, $R^2$, $R^4$ and $R^5$ are as defined above, $R^{17}$ to $R^{20}$ (substituent X) are each independently hydrogen, halogen, $C_1$-$C_{10}$ alkyl, or $C_1$-$C_{10}$ alkoxy group, $R^{25}$ to $R^{30}$ (substituent X) are each independently hydrogen or a substituted or unsubstituted, $C_1$-$C_{20}$ monovalent hydrocarbon group. Preferably $R^{17}$ to $R^{20}$ and $R^{25}$ to $R^{30}$ are hydrogen.

Suitable monovalent hydrocarbon groups include alkyl, aryl and aralkyl groups, examples of which are as exemplified above.

Examples of the alkyl group, alkoxy group and halogen are as exemplified above.

$L^1$ is at least one two-electron ligand wherein two electrons in the ligand coordinate with iron, selected from isonitrile, amine, imine, nitrogen-containing heterocyclic ring, phosphine, phosphite and sulfide.

The coordination number $m^1$ of two-electron ligands $L^1$ is an integer of 1 to 4, preferably 2. It is noted that when $m^1$ is 2 to 4, two ligands $L^1$ may bond together.

Examples of the isonitrile include those represented by RNC wherein R is each independently as defined above.

Examples of the amine include tertiary amines represented by $R_3N$ wherein R is each independently as defined above.

Examples of the imine include those represented by RC(=NR)R wherein R is each independently as defined above.

Examples of the nitrogen-containing heterocycle include pyrrole, imidazole, pyridine, pyrimidine, oxazoline, and isooxazoline.

Examples of the phosphine include those of $R_3P$ wherein R is each independently as defined above.

Examples of the phosphite include those of $(RO)_3P$ wherein R is each independently as defined above.

Examples of the sulfide include those of RSR wherein R is each independently as defined above.

Of the foregoing, the two-electron ligand $L^1$ is more preferably at least one selected from isonitrile, nitrogen-containing heterocycle, and phosphine, most preferably isonitrile having the same electron arrangement as carbon monoxide.

As described above, exemplary of the isonitrile are those represented by RNC wherein R is each independently as defined above. Preferred are those wherein R is a substituted or unsubstituted, $C_1$-$C_{10}$ alkyl group, $C_6$-$C_{20}$ aryl group or $C_7$-$C_{20}$ aralkyl group, more preferably $C_6$-$C_{10}$ aryl group, and even more preferably phenyl group having a substituent such as $C_1$-$C_{10}$ alkyl.

Examples of the isonitrile which can be used herein include, but are not limited to, alkyl isocyanides such as methylisocyanide, ethyl isocyanide, n-propyl isocyanide, cyclopropyl isocyanide, n-butyl isocyanide, isobutyl isocyanide, sec-butyl isocyanide, t-butyl isocyanide, n-pentyl isocyanide, isopentyl isocyanide, neopentyl isocyanide, n-hexyl isocyanide, cyclohexyl isocyanide, cycloheptyl isocyanide, 1,1-dimethylhexyl isocyanide, 1-adamantyl isocyanide, and 2-adamantyl isocyanide; aryl isocyanides such as phenyl isocyanide, 2-methylphenyl isocyanide, 4-methylphenyl isocyanide, 2,4-dimethylphenyl isocyanide, 2,5-dimethylphenyl isocyanide, 2,6-dimethylphenyl isocyanide, 2,4,6-trimethylphenyl isocyanide, 2,4,6-tri-t-butylphenyl isocyanide, 2,6-diisopropylphenyl isocyanide, 1-naphthyl isocyanide, 2-naphthyl isocyanide, and 2-methyl-1-naphthyl isocyanide; and aralkyl isocyanides such as benzyl isocyanide and phenylethyl isocyanide.

Examples of the nitrogen-containing heterocycle are as described above, with pyridine ring being preferred.

Examples of the pyridine ring-containing compound which can be used herein include, but are not limited to, pyridines such as pyridine, 2-methylpyridine, 3-methylpyridine, 4-methylpyridine, and 2,6-dimethylpyridine; and bipyridines such as 2,2'-bipyridine, 4,4'-dimethyl-2,2'-bipyridine, 5,5'-dimethyl-2,2'-bipyridine, 4,4'-diethyl-2,2'-bipyridine, and 4,4'-di-t-butyl-2,2'-bipyridine.

As described above, examples of the phosphite include those of $(RO)_3P$ wherein R is each independently as defined above. Preferred are those wherein R is a substituted or unsubstituted, $C_1$-$C_{10}$ alkyl group or $C_6$-$C_{20}$ aryl group, more preferably $C_1$-$C_{10}$ alkyl group.

Examples of the phosphite compound which can be used herein include, but are not limited to, trialkyl phosphites such as trimethyl phosphite, triethyl phosphite, triisopropyl phosphite, tri-n-butyl phosphite, tris(2-ethylhexyl) phosphite, tri-n-decyl phosphite, 4-methyl-2,6,7-trioxa-1-phosphabicyclo[2.2.2]octane (trimethylol ethane cyclic phosphite), and 4-ethyl-2,6,7-trioxa-1-phosphabicyclo[2.2.2] octane (trimethylol propane phosphite); and triaryl phosphites such as triphenyl phosphite.

On the other hand, $L^2$ is a two-electron ligand other than CO and $L^1$. The two-electron ligand is not particularly limited as long as CO ligand and $L^1$ are excluded. Use may be made of any ligands which are conventionally used as the two-electron ligand in metal complexes. Typical ligands include compounds of nitrogen, oxygen, sulfur, phosphorus, and other elements containing an unshared electron pair (unpaired electron) such as amine, imine, nitrogen-containing heterocycle, phosphine, phosphite, arsine, alcohol, thiol, ether, and sulfide; compounds containing π-electron such as alkene and alkyne; compounds containing both unpaired electron and π-electron such as aldehyde, ketone, nitrile, and isonitrile; molecular hydrogen (σ-electron in H—H bond coordinates) and hydrosilane (σ-electron in Si—H bond coordinates) capable of bonding by agostic interaction.

Examples of the amine, imine, nitrogen-containing heterocycle, phosphine, phosphite, sulfide and isonitrile compounds are as exemplified above for $L^1$.

Examples of the arsine include those of $R_3As$ wherein R is each independently as defined above.

Examples of the alcohol include those of ROH wherein R is as defined above.

Examples of the thiol include the above alcohols in which oxygen atom is replaced by sulfur atom.

Included in the ether are those represented by ROR wherein R is each independently as defined above.

Included in the ketone are those represented by RCOR wherein R is each independently as defined above.

Included in the alkene are those of 2 to 30 carbon atoms such as ethene, propene, 1-butene, 2-butene, 1-pentene, 2-pentene, cyclopentene, 1-hexene, cyclohexene, 1-heptene, 1-octene, 1-nonene, and 1-decene.

Included in the alkyne are those of 2 to 30 carbon atoms such as ethyne, propyne, 1-butyne, 2-butyne, 1-pentyne, 2-pentyne, 1-hexyne, 1-heptyne, 1-octyne, 1-nonyne, and 1-decyne.

Examples of the hydrosilane include triorganohydrosilanes, specifically tri($C_1$-$C_{30}$ organo)hydrosilanes, for example, those of $R^1R^2R^3SiH$ wherein $R^1$ to $R^3$ are as defined above.

As the two-electron ligand $L^2$ used herein, a ligand which forms a relatively weak bond with iron is advantageous in terms of catalytic activity. Among the above examples, thiol, sulfide, and triorganohydrosilane compounds are more preferable, and two triorganohydrosilanes represented by $SiHR^7R^8R^9$ and $SiHR^{10}R^{11}R^{12}$ wherein $R^7$ to $R^{12}$ are each independently an alkyl, aryl or aralkyl group which may be substituted with X which is as defined above are even more preferable.

Examples of the alkyl, aryl and aralkyl groups are the same as exemplified above. Inter alia, $C_1$-$C_{10}$ alkyl groups, $C_6$-$C_{20}$ aryl groups, and $C_7$-$C_{20}$ aralkyl groups are preferred, with $C_1$-$C_{10}$ alkyl groups and $C_6$-$C_{20}$ aryl groups being more preferred.

The coordination number $m^2$ of two-electron ligands $L^2$ is an integer of 0 to 3, preferably 2. Also $m^1+m^2$ is equal to 3 or 4, preferably 4. It is noted that when $m^2$ is 2 or 3, two ligands $L^2$ may bond together. Typical examples include, but are not limited to, ethylenediamine, ethylene glycol dimethyl ether, 1,3-butadiene, and those of the formulae shown below.

In the mononuclear iron complex, it is excluded that three of ligands $L^1$ and $L^2$ bond together to form a ligand containing three coordinating two-electron functional groups, for example, $\eta^6$-arylene structure.

[Chemical Formula 5]

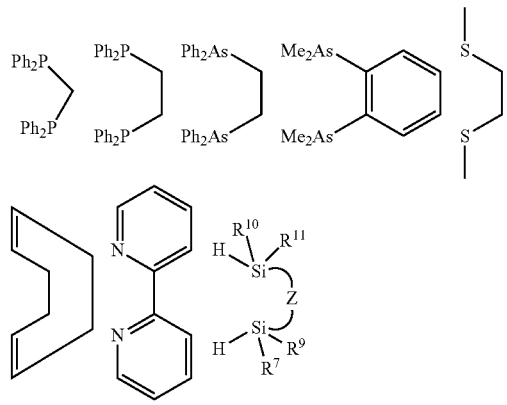

Herein Me stands for methyl, and Ph for phenyl. $R^7$, $R^9$, $R^{10}$, $R^{11}$ and Z are as defined above.

It is noted that in the mononuclear iron complex of formula (1), when two ligands $L^1$ and two ligands $L^2$ (which are distinguishably represented by $L^{2a}$ and $L^{2b}$) are contained, for example, there exist coordination geometry isomers as depicted by the following formulae. The mononuclear iron complex encompasses all such coordination geometry isomers.

[Chemical Formula 6]

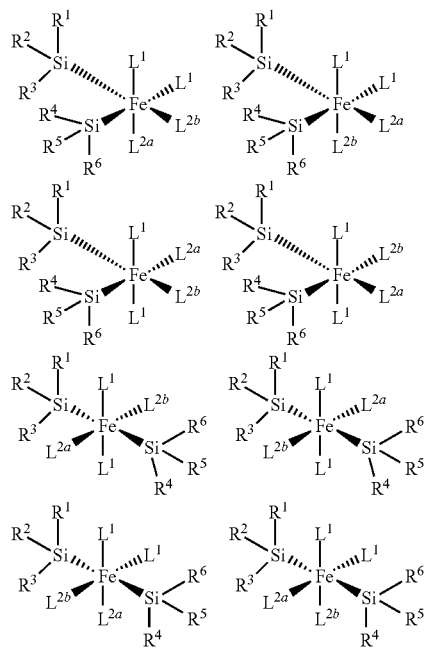

Herein $R^1$ to $R^6$ and $L^1$ are as defined above, $L^{2a}$ and $L^{2b}$ have the same meaning as $L^2$.

When ligands $L^2$ are triorganohydrosilanes of $SiHR^7R^8R^9$ and $SiHR^{10}R^{11}R^{12}$ wherein $R^7$ to $R^{12}$ are as defined above, at least two of four silicon atoms in the mononuclear iron complex may be linked by the crosslinking substituent Z. A combination of silicon atoms may be either a combination of silicon atoms having a silicon-iron covalent bond, a combination of silicon atoms in Si—H coordination, or a combination of a silicon-iron covalent bond with a silicon atom in Si—H coordination. Herein, the number of Z linking two silicon atoms is 1 to 3 whereas the total number of Z in the overall complex is 1 to 12.

When a mononuclear iron complex having crosslinking substituent Z is represented by a single coordination geometry, exemplary geometries are those of the following formulae, but not limited thereto. As alluded to previously, there are present coordination geometry isomers other than the illustrated ones, and in such cases, similar geometries having crosslinking substituent Z are present.

[Chemical Formula 7]

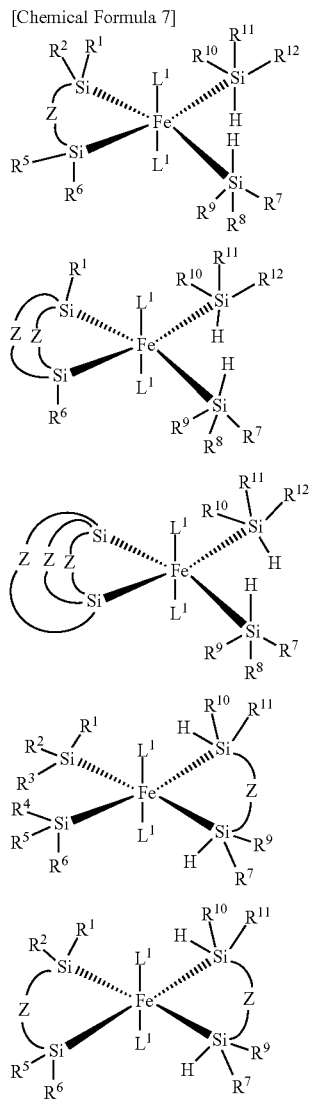

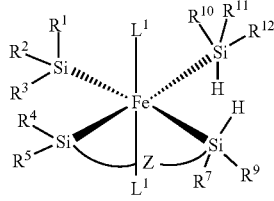

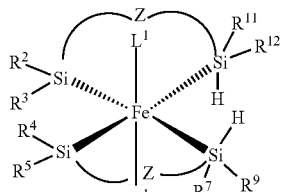

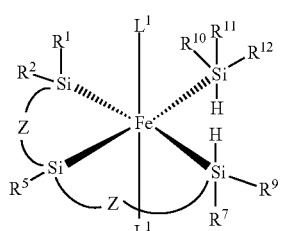

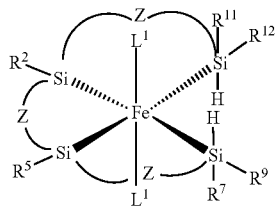

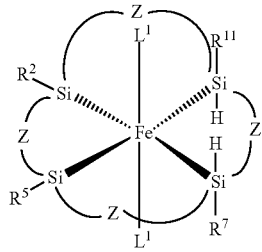

Herein $R^1$ to $R^{12}$, $L^1$ and Z are as defined above.

Exemplary geometries of the mononuclear iron complex having disilametallacycle structure include those of the following formulae (depicted with $L^1$ omitted), but are not limited thereto.

[Chemical Formula 8]

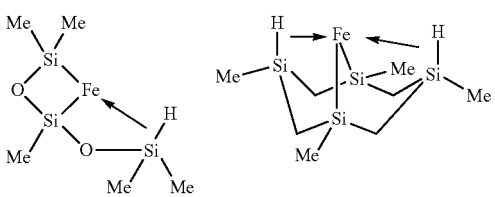

-continued

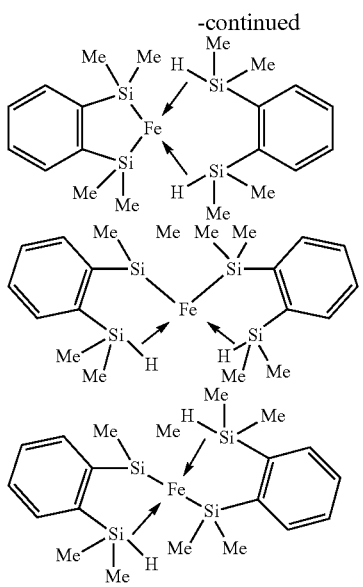

Herein Me stands for methyl.

Especially preferred in the invention are mononuclear iron complexes having two ligands $L^1$ coordinated and triorganohydrosilanes (as two-electron ligand) in agostic Si—H bond coordination. When such an iron complex is represented for convenience sake by a single coordination geometry, one exemplary geometry is represented by the formula (2). As alluded to previously, other coordination geometry isomers are acceptable.

[Chemical Formula 9]

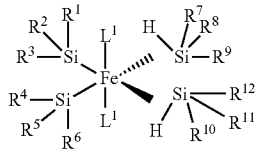

(2)

Herein $L^1$ is as defined above.

In formula (2), $R^1$ to $R^{12}$ are as defined above. Preferably $R^1$ to $R^6$ are each independently an alkyl, aryl or aralkyl group which may be substituted with X which is as defined above.

Examples of the alkyl, aryl and aralkyl groups are the same as exemplified above, while $C_1$-$C_{10}$ alkyl, $C_6$-$C_{20}$ aryl and $C_7$-$C_{20}$ aralkyl groups are preferred, and $C_1$-$C_{10}$ alkyl and $C_6$-$C_{20}$ aryl groups are more preferred.

In formula (2) as well, at least two of four silicon atoms in the mononuclear iron complex may be linked by the crosslinking substituent. Specifically, at least one pair of any one of $R^1$ to $R^3$ and any one of $R^4$ to $R^6$ or any one of $R^7$ to $R^9$, or at least one pair of any one of $R^{10}$ to $R^{12}$ and any one of $R^4$ to $R^6$ or any one of $R^7$ to $R^9$ may bond together to form a crosslinking substituent such as alkylene, arylene or aralkylene. Alternatively, at least one pair of any one of $R^1$ to $R^3$ and any one of $R^4$ to $R^6$ or any one of $R^7$ to $R^9$ may bond together to form a crosslinking substituent such as alkylene, arylene or aralkylene, and at least one pair of any one of $R^{10}$ to $R^{12}$ and any one of $R^4$ to $R^6$ or any one of $R^7$ to $R^9$ may bond together to form a crosslinking substituent such as alkylene, arylene or aralkylene.

Examples of the alkylene, arylene and aralkylene groups are the same as exemplified above, while $C_1$-$C_{10}$ alkylene, $C_7$-$C_{20}$ arylene and $C_7$-$C_{20}$ aralkylene groups are preferred, and $C_1$-$C_6$ alkylene and $C_7$-$C_{20}$ arylene groups are more preferred.

When the mononuclear iron complex which can be advantageously used herein is represented by a typical coordination geometry, those of the formula (3) or (4) are included. Specifically those of the formulae (5) to (10) are included, and more specifically complexes A to C are preferred. The complexes are not limited thereto, and coordination geometry isomers thereof may also be advantageously used.

[Chemical Formula 10]

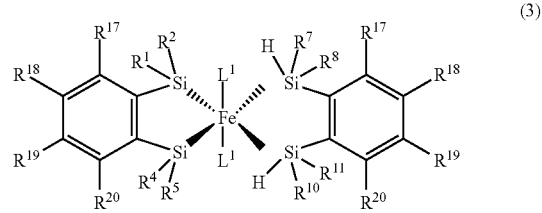

(3)

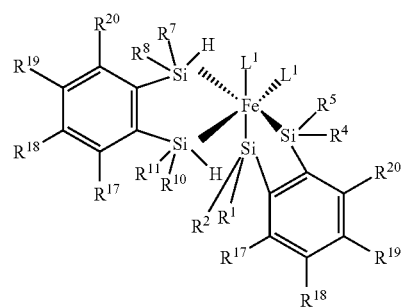

(4)

Herein, $R^1$, $R^2$, $R^4$, $R^5$, $R^7$, $R^8$, $R^{10}$, $R^{11}$, $R^{17}$ to $R^{20}$, and $L^1$ are as defined above.

[Chemical Formula 11]

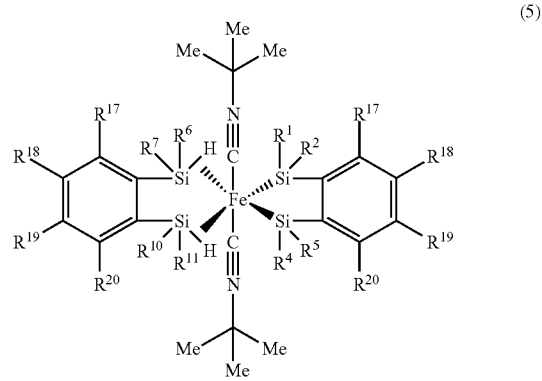

(5)

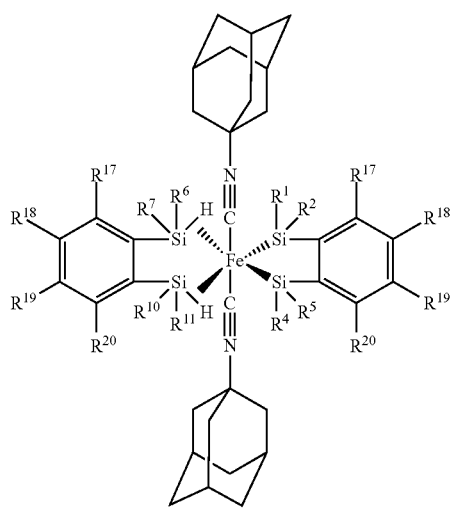
(6)
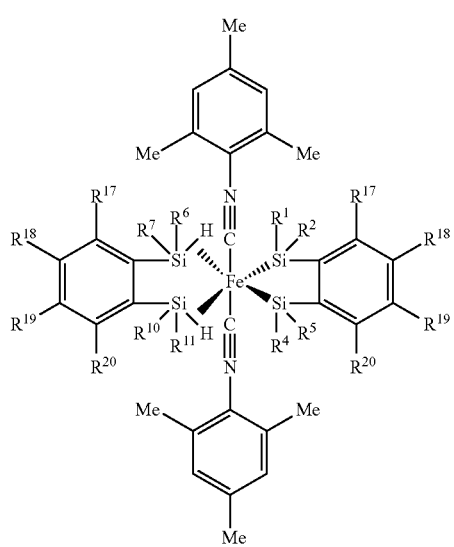
(7)
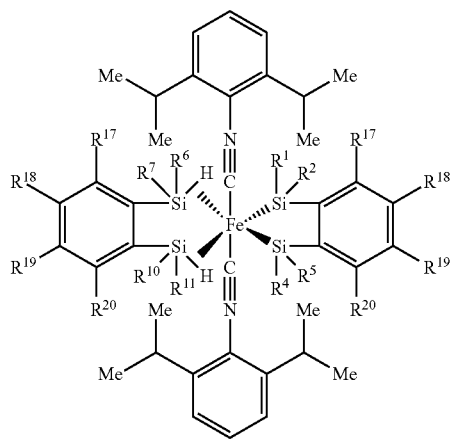
(8)
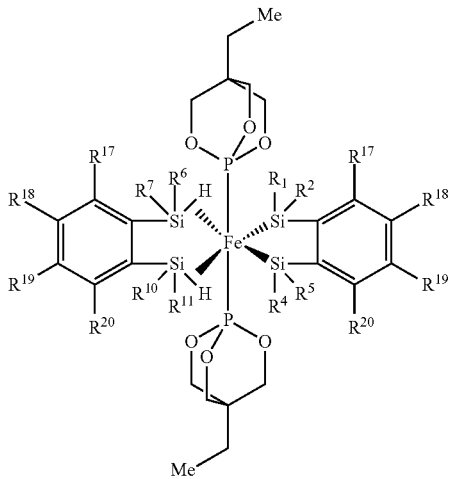
(9)
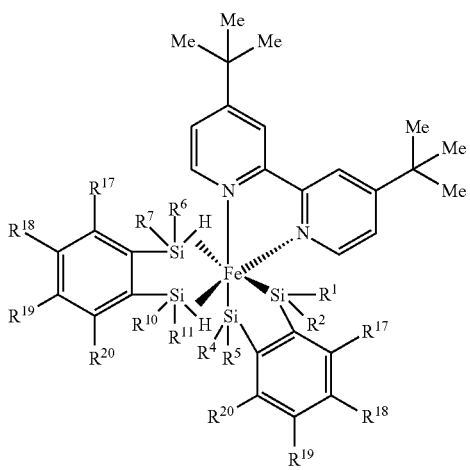
(10)
Herein, $R^1$, $R^2$, $R^4$, $R^5$, $R^6$, $R^7$, $R^{10}$, $R^{11}$, $R^{17}$ to $R^{20}$ are as defined above, and Me stands for methyl.
[Chemical Formula 12]
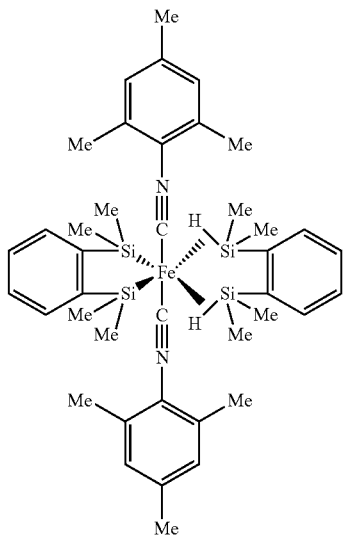
A -continued

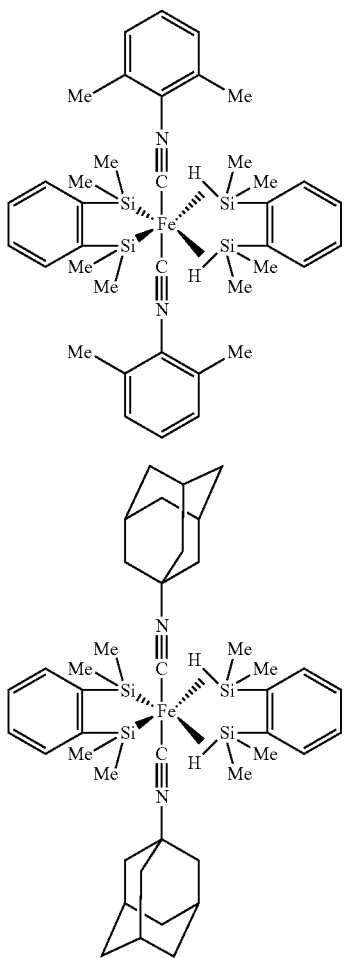

Herein Me stands for methyl.

The mononuclear iron complex of the invention may be prepared by any combination of well-known organic synthetic reactions.

For example, the iron complex A, B or C may be obtained by reacting an iron-olefin complex having a cycloalkadienyl group such as cyclohexadienyl or cyclooctadienyl and an alkenyl group such as allyl or 2-methylallyl as ligands with a bissilyl compound such as 1,2-bis(dimethylsilyl)benzene, isonitrile compound such as t-butyl isocyanide, phosphite compound, or bipyridine compound in an organic solvent in an inert gas atmosphere such as argon gas.

In this case, the amount of the bissilyl compound used may be about 1 to 10 moles, preferably 2 to 5 moles per mole of the iron-olefin complex.

The amount of the isonitrile compound, phosphite compound or bipyridine compound used may be about 1 to 10 moles, preferably 2 to 5 moles per mole of the iron-olefin complex.

As the organic solvent, any solvents may be used as long as they do not adversely affect the reaction. Suitable solvents used herein include aliphatic hydrocarbons such as pentane, hexane, heptane, octane, and cyclohexane; ethers such as diethyl ether, diisopropyl ether, dibutyl ether, cyclopentyl methyl ether, tetrahydrofuran, and 1,4-dioxane; and aromatic hydrocarbons such as benzene, toluene, xylene and mesitylene.

The reaction temperature may be set as appropriate in the range from the melting point to the boiling point of the organic solvent, preferably in the range of 10 to 100° C., and more preferably 30 to 80° C.

The reaction time is typically about 1 to about 48 hours.

After the completion of reaction, the solvent is distilled off, whereupon the target compound may be isolated by well-known purifying means such as recrystallization. Without isolation, the iron complex as prepared may be used as a catalyst for the intended reaction.

As alluded to previously, the mononuclear iron complexes of the invention display catalytic activity to at least one of hydrosilylation reaction, hydrogenation reaction, and reductive reaction of carbonyl compounds. Some complexes display catalytic activity to two reactions, and certain complexes display catalytic activity to all three reactions.

For hydrosilylation reaction between a compound having an aliphatic unsaturated bond such as an olefin, silane or organopolysiloxane compound and a silane or organopolysiloxane compound having a Si—H bond in the presence of the inventive mononuclear iron complex as catalyst, the amount of the catalyst used, though not particularly limited, is preferably at least 0.005 mol % when it is taken into account that the target compound is obtained in high yields by driving reaction under mild conditions at room temperature to about 100° C.

When an olefin compound having an aliphatic unsaturated bond is reduced with hydrogen gas in the presence of the inventive mononuclear iron complex as catalyst, to produce a saturated compound, the amount of the catalyst used, though not particularly limited, is preferably at least 0.05 mol % when it is taken into account that the target compound is obtained in high yields by driving reaction under mild conditions at room temperature and a hydrogen pressure of about 1 atm.

Also, when a carbonyl compound is reduced with a silane or siloxane compound having an Si—H group in the presence of the inventive mononuclear iron complex as catalyst, the amount of the catalyst used, though not particularly limited, is preferably at least 0.1 mol % when it is taken into account that the target compound is obtained in high yields by driving reaction under mild conditions.

Examples of the carbonyl compound which can be subjected to reductive reaction include compounds having an amide, aldehyde, ketone, ester, carboxylic acid, and carboxylic acid salt (e.g., sodium or potassium salt) group. The carbonyl compound can be converted to a corresponding amine or alcohol compound by reacting it with a silane or siloxane having an Si—H group in the presence of the inventive iron complex catalyst.

In any reactions, the upper limit of the amount of the catalyst used is about 5 mol % from the economic aspect, though not critical.

EXAMPLES

Examples of the invention are given below by way of illustration and not by way of limitation.

For synthesis of iron complexes, a Schlenk system or glovebox was used, and all steps were performed in argon atmosphere. All the solvents used in the preparation of transition metal compounds were deoxygenated and dried by well-known techniques prior to use.

Hydrosilylation reaction of alkene, hydrogenation reaction, reductive reaction of amide, and solvent purification were all performed in an inert gas atmosphere. All the solvents and ingredients used in these reactions were purified, dried and deoxygenated by well-known techniques prior to use.

Analyses of $^1$H and $^{13}$C-NMR were performed by JNM-ECA600 and JNM-LA400 (JEOL Ltd.); IR spectroscopy by FT/IR-550 (JASCO Corp.); elemental analysis by 2400II/CHN (Perkin Elmer); X-ray crystallography by VariMax (Rigaku Corp.) with MoK α-ray of 0.71069 angstrom.

It is noted that in the chemical structural formulae shown below, hydrogen atoms are omitted according to the standard nomenclature. Me stands for methyl.

(1) Synthesis of Iron Complex

[Example 1] Synthesis of Iron Complex A

[Chemical Formula 13]

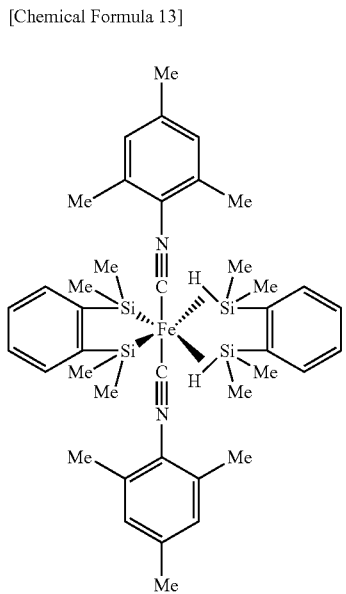

Herein Me stands for methyl.

A 100-mL Schlenk tube under argon atmosphere was charged with ($\eta^6$-1,3,5,7-cyclooctatetraene)($\eta^4$-1,3,5,7-cyclooctatetraene)iron(0) complex (40 mg, 0.15 mmol) and 2,4,6-trimethylphenyl isocyanide (66 mg, 0.45 mmol), to which hexane (40 mL) which had been deaerated and dried was added. The contents were stirred at room temperature for 1 hour, after which 1,2-bis(dimethylsilyl)benzene (64 mg, 0.33 mmol) was added. The reactor interior was purged with hydrogen atmosphere. Under light irradiation using a high-pressure mercury lamp (UM-453B-A, 450 W, by Ushio Inc.), the contents were stirred at room temperature for 48 hours. After the completion of reaction, the reaction mixture was dried in vacuum. The dry product was dissolved in toluene (10 mL), from which a small amount of black insoluble matter as by-product was removed by centrifugation. Thereafter, the toluene solution was dried in vacuum, yielding iron complex A (36 mg, 0.05 mmol, 35%) typically represented by the above formula.

Figure 2:
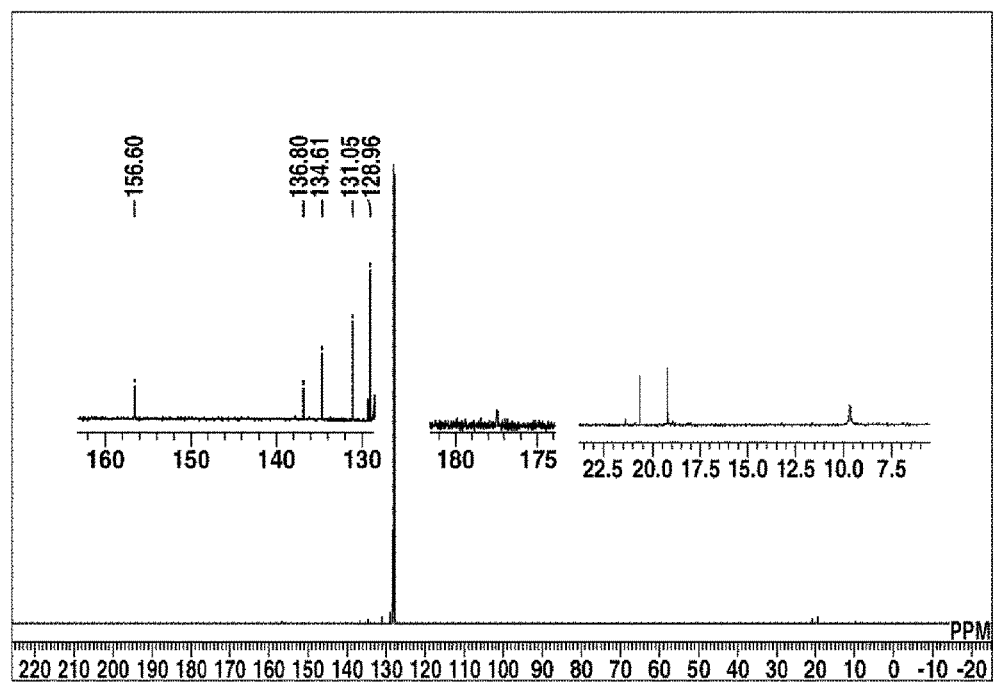
FIG. 2 is a diagram showing $^{13}$C-NMR spectrum of iron complex A in Example 1.

For the resulting iron complex A, the measurement results of $^1$H-NMR are shown in FIG. 1, and the measurement results of $^{13}$C-NMR in FIG. 2.

$^1$H-NMR (C$_6$D$_6$, 600 MHz)
δ=−11.54 (s, J$_{Si-H}$=14.7 Hz, 2H, Si—H), 0.90 (s, 24H, SiMe$_2$), 1.82 (s, 6H, Me), 1.91 (s, 12H, C$_6$H$_3$Me$_2$), 6.30 (s, 4H, C$_6$H$_2$), 7.29-7.33 (m, 4H, C$_6$H$_4$), 7.71-7.75 (m, 4H, C$_6$H$_4$)

$^{13}$C-NMR (C$_6$D$_6$, 150 MHz)
δ=9.70 (s, SiMe$_2$), 19.2 (s, C$_6$H$_2$Me$_3$), 20.7 (s, C$_6$H$_2$Me$_3$), 129.0 (s, Ph), 129.3 (s, Ph), 131.1 (s, Ph), 131.6 (s, Ph), 134.6 (s, Ph), 136.8 (s, Ph), 156.6 (s, ipso of C$_6$H$_4$), 177.5 (s, CN-Mes)

IR (KBr pellet): ν=1958 (ν$_{Si-H}$), 2056 (ν$_{Fe-CN}$) cm$^{-1}$
Anal. calcd. for C$_{40}$H$_{56}$N$_2$FeSi$_4$: C 65.54, H 7.70, N 3.82. Found: C 65.32, H 7.48, N 3.67.

[Example 2] Synthesis of Iron Complex B

[Chemical Formula 14]

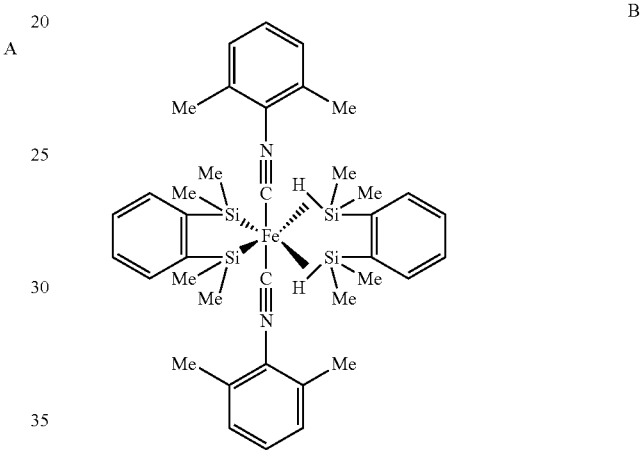

Herein Me stands for methyl.

A 100-mL Schlenk tube under argon atmosphere was charged with ($\eta^6$-1,3,5,7-cyclooctatetraene)($\eta^4$-1,3,5,7-cyclooctatetraene)iron(0) complex (100 mg, 0.38 mmol) and 2,6-dimethylphenyl isocyanide (149 mg, 1.14 mmol), to which hexane (60 mL) which had been deaerated and dried was added. The contents were stirred at room temperature for 1 hour, after which 1,2-bis(dimethylsilyl)benzene (162 mg, 0.83 mmol) was added. The reactor interior was purged with hydrogen atmosphere. Under light irradiation using a high-pressure mercury lamp (UM-453B-A, 450 W, by Ushio Inc.), the contents were stirred at room temperature for 48 hours. After the completion of reaction, the reaction mixture was dried in vacuum. The dry product was dissolved in toluene (10 mL), from which a small amount of black insoluble matter as by-product was removed by centrifugation. Thereafter, the toluene solution was dried in vacuum, yielding iron complex B (115 mg, 0.16 mmol, 43%) typically represented by the above formula.

Figure 3:
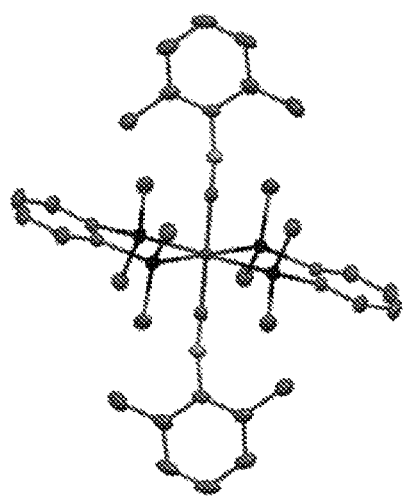
FIG. 3 illustrates the geometry of iron complex B obtained in Example 2.
Figure 4:
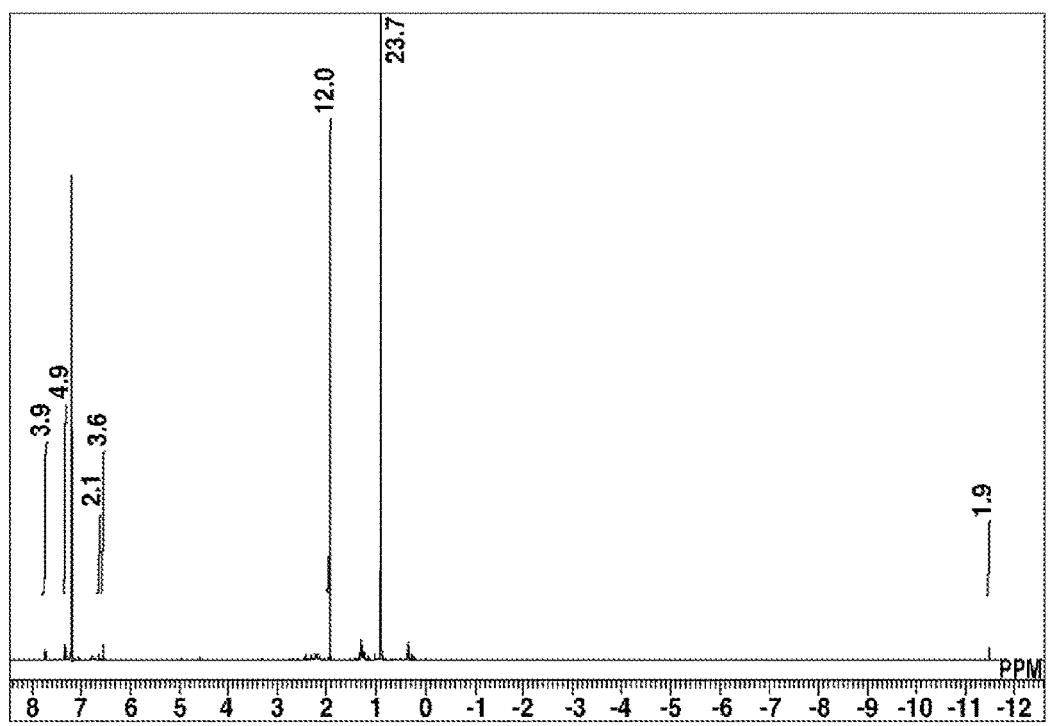
FIG. 4 is a diagram showing $^1$H-NMR spectrum of iron complex B in Example 2.

For the resulting iron complex B, the geometry is shown in FIG. 3, and the measurement results of $^1$H-NMR in FIG. 4.

$^1$H-NMR (C$_6$D$_6$, 600 MHz)
δ=−11.48 (s, J$_{Si-H}$=16.1 Hz, 2H, Si—H), 0.90 (s, 24H, SiMe$_2$), 1.94 (s, 12H, C$_6$H$_3$Me$_2$), 6.53-6.58 (m, 4H, C$_6$H$_3$Me$_2$), 6.62-6.66 (m, 2H, C$_6$H$_3$Me$_2$), 7.31-7.35 (m, 4H, C$_6$H$_4$), 7.71-7.76 (m, 4H, C$_6$H$_4$)

IR (KBr pellet): ν=1960 (ν$_{Si-H}$), 2052 (ν$_{Fe-CN}$) cm$^{-1}$
Anal. calcd. for C$_{38}$H$_{52}$N$_2$FeSi$_4$: C 64.74, H 7.43, N 3.97. Found: C 64.56, H 7.24, N 3.87.

[Example 3] Synthesis of Iron Complex C

[Chemical Formula 15]

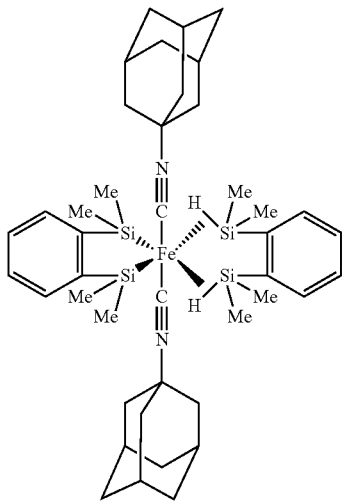

Herein Me stands for methyl.

A 100-mL Schlenk tube under argon atmosphere was charged with ($\eta^6$-1,3,5,7-cyclooctatetraene)($\eta^4$-1,3,5,7-cyclooctatetraene)iron(0) complex (50 mg, 0.19 mmol) and adamantyl isocyanide (92 mg, 0.57 mmol), to which hexane (50 mL) which had been deaerated and dried was added. The contents were stirred at room temperature for 1 hour, after which 1,2-bis(dimethylsilyl)benzene (80 mg, 0.42 mmol) was added. The reactor interior was purged with hydrogen atmosphere. Under light irradiation using a high-pressure mercury lamp (UM-453B-A, 450 W, by Ushio Inc.), the contents were stirred at room temperature for 48 hours. After the completion of reaction, the reaction mixture was dried in vacuum. The dry product was dissolved in toluene (5 mL), from which a small amount of black insoluble matter as by-product was removed by centrifugation. Thereafter, the toluene solution was dried in vacuum, yielding iron complex C (55 mg, 0.07 mmol, 38%) typically represented by the above formula.

Figure 5:
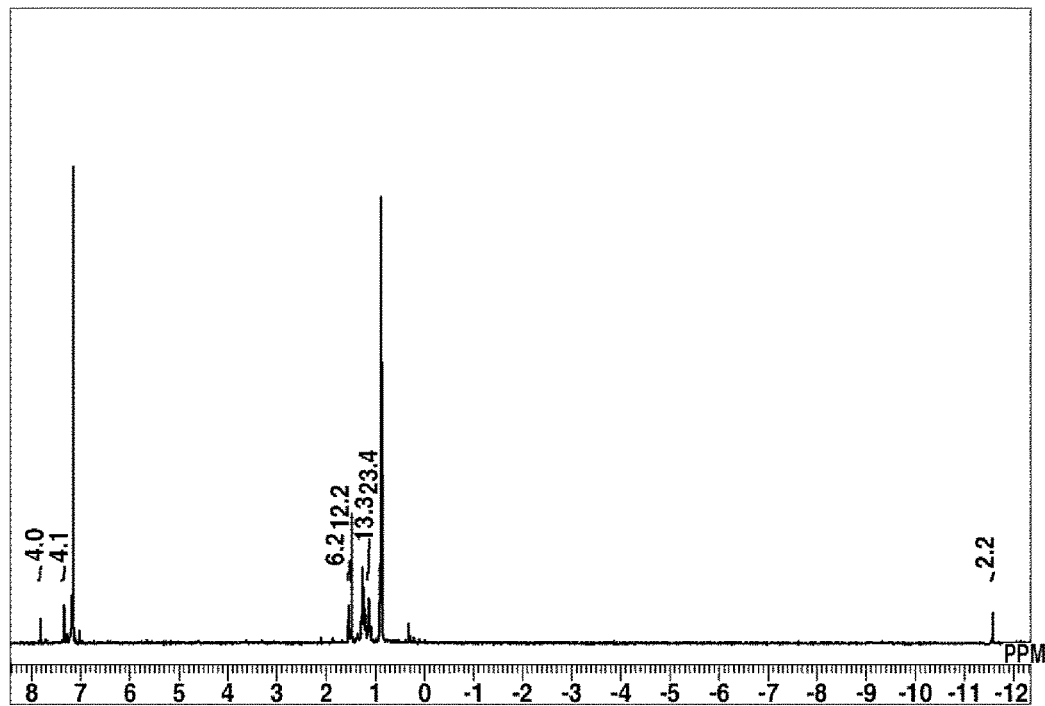
FIG. 5 is a diagram showing $^1$H-NMR spectrum of iron complex C in Example 3.

For the resulting iron complex C, the measurement results of $^1$H-NMR are shown in FIG. 5.

$^1$H-NMR (C$_6$D$_6$, 600 MHz)

δ=−11.57 (s, J$_{Si-H}$=13.1 Hz, 2H, Si—H), 0.88 (s, 24H, SiMe$_2$), 1.08-1.16 (m, 12H, CH$_2$), 1.47-1.49 (m, 12H, CH$_2$), 1.51-1.55 (m, 6H, CH), 7.32-7.35 (m, 4H, C$_6$H$_4$), 7.79-7.84 (m, 4H, C$_6$H$_4$)

IR (KBr pellet): ν=1987 (ν$_{Si-H}$), 2073 (ν$_{Ru-CN}$) cm$^{-1}$ (2) Hydrosilylation Using Iron Complex

[Chemical Formula 16]

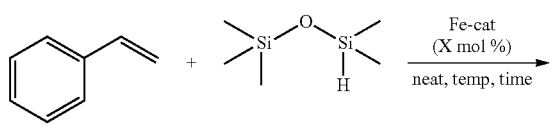

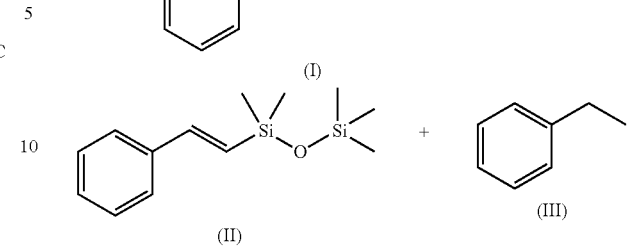

[Example 4] Hydrosilylation Reaction of Styrene with 1,1,1,3,3-pentamethyldisiloxane Using Iron Complex A A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst. To the tube, styrene (104 mg, 1.0 mmol) was added, after which 1,1,1,3,3-pentamethyldisiloxane (163 mg, 1.1 mmol) was added. The solution was stirred at 50° C. for 23 hours. The solution was cooled, to which anisole (108 mg, 1.0 mmol) was added as internal standard. By $^1$H-NMR spectroscopy, the geometry and yield of the product were determined. The results are shown as Entry 1 in Table 1.

1,1,1,3,3-pentamethyl-3-[(1E)-2-phenylethenyl]-disiloxane (Table 1, Compound (II))

$^1$H-NMR (400 MHz, CDCl$_3$)
δ=0.11 (s, 6H, Si(CH$_3$)$_2$), 0.22 (s, 9H, Si(CH$_3$)$_3$), 6.42 (d, J$_{H-H}$=19.3 Hz, 1H, —CH═CH—), 6.93 (d, J$_{H-H}$=19.3 Hz, 1H, —CH═CH—), 7.24-7.29 (m, 1H, C$_6$H$_5$), 7.31-7.39 (m, 2H, C$_6$H$_5$), 7.43-7.47 (m, 2H, C$_6$H$_5$)

Ethylbenzene (Table 1, Compound (III))
$^1$H-NMR (400 MHz, CDCl$_3$)
δ=1.26 (t, 2H, J$_{H-H}$=7.7 Hz, CH$_3$), 2.67 (q, 2H, J$_{H-H}$=7.7 Hz, CH$_2$), 7.16-7.24 (m, 3H, C$_6$H$_5$), 7.27-7.33 (m, 2H, C$_6$H$_5$)

[Example 5] Hydrosilylation Reaction of Styrene with 1,1,1,3,3-pentamethyldisiloxane Using Iron Complex B A 20-mL Schlenk tube equipped with a magnetic stirrer was heat dried while pumping to a vacuum of 5 Pa before its interior was purged with argon atmosphere. Into the Schlenk tube, iron complex B (7.1 mg, 0.01 mmol) was admitted as catalyst. To the tube, styrene (104 mg, 1.0 mmol) was added, after which 1,1,1,3,3-pentamethyldisiloxane (163 mg, 1.1 mmol) was added. The solution was stirred at 50° C. for 23 hours. The solution was cooled, to which anisole (108 mg, 1.0 mmol) was added as internal standard. By $^1$H-NMR spectroscopy, the geometry and yield of the product were determined. The results are shown as Entry 2 in Table 1.

[Example 6] Hydrosilylation Reaction of Styrene with 1,1,1,3,3-pentamethyldisiloxane Using Iron Complex C A 20-mL Schlenk tube equipped with a magnetic stirrer was heat dried while pumping to a vacuum of 5 Pa before its interior was purged with argon atmosphere. Into the Schlenk tube, iron complex C (7.7 mg, 0.01 mmol) was admitted as catalyst. To the tube, styrene (104 mg, 1.0 mmol) was added, after which 1,1,1,3,3-pentamethyldisiloxane (163 mg, 1.1 mmol) and dimethoxyethane (3.6 mg, 0.04 mmol) were added. The solution was stirred at 80° C. for 24 hours. The solution was cooled, to which anisole (108 mg, 1.0 mmol) was added as internal standard. By $^1$H-NMR spectroscopy, the geometry and yield of the product were determined. The results are shown as Entry 3 in Table 1.

1,1,1,3,3-pentamethyl-3-(2-phenylethyl)-disiloxane
(Table 1, Compound (I))

$^1$H-NMR (400 MHz, CDCl$_3$)

δ=−0.03 (s, 6H, Si(CH$_3$)$_2$), −0.02 (s, 9H, Si(CH$_3$)$_3$), 0.775-0.81 (m, 2H, SiCH$_2$), 2.52-2.57 (m, 2H, CH$_2$C$_6$H$_5$), 7.09-7.13 (m, 2H, C$_6$H$_5$), 7.17-7.22 (m, 3H, C$_6$H$_5$)

TABLE 1

| Entry | Cat | Cat loading (x) (mol %) | Temp. (° C.) | Time (h) | Yield (I) | (II) | (III) |
|---|---|---|---|---|---|---|---|
| 1 | A | 1 | 50 | 23 | 0 | 30 | 35 |
| 2 | B | 1 | 50 | 23 | 0 | 36 | 34 |
| 3[a] | C | 1 | 80 | 24 | 20 | 2 | 2 |

[a]reaction performed in the presence of 4 equivalents of dimethoxyethane relative to iron (3) Hydrogenation Reaction of 1-octene Using Iron Complex

[Chemical Formula 17]

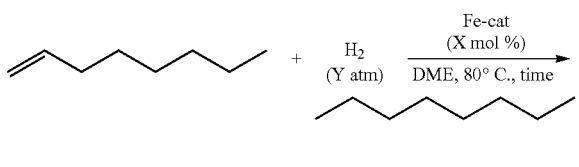

[Example 7] Hydrogenation Reaction of 1-octene Using Iron Complex A

A 20-mL Schlenk tube equipped with a magnetic stirrer was heat dried while pumping to a vacuum of 5 Pa before its interior was purged with argon atmosphere. Into the Schlenk tube, iron complex A (3.7 mg, 0.005 mmol) was admitted as catalyst and dissolved in dimethoxyethane (2 mL). To the solution, 1-octene (112 mg, 1.0 mmol) was added. The Schlenk tube was then purged with hydrogen. In a hydrogen atmosphere of 1 atm., the solution was stirred at 80° C. for 2 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 1 in Table 2.

$^1$H-NMR (CDCl$_3$, 400 MHz)

δ=0.88 (t, J$_{HH}$=7.2 Hz, 6H, CH$_3$), 1.16-1.36 (m, 12H, —(CH$_2$)$_6$—)

$^{13}$C-NMR (100 MHz, CDCl$_3$)

δ=14.27, 22.86, 29.48, 32.10

[Example 8] Hydrogenation Reaction Using a Low Catalyst Concentration of Iron Complex A A 20-mL Schlenk tube equipped with a magnetic stirrer was heat dried while pumping to a vacuum of 5 Pa before its interior was purged with argon atmosphere. Into the Schlenk tube, iron complex A (3.7 mg, 0.005 mmol) was admitted as catalyst and dissolved in dimethoxyethane (2 mL). To the solution, 1-octene (1.12 g, 10 mmol) was added. The solution was transferred into an autoclave, whose interior was purged with hydrogen. In a hydrogen atmosphere of 20 atm., the solution was stirred at 80° C. for 6 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 2 in Table 2.

[Example 9] Hydrogenation Reaction Using Iron Complex B

A 20-mL Schlenk tube equipped with a magnetic stirrer was heat dried while pumping to a vacuum of 5 Pa before its interior was purged with argon atmosphere. Into the Schlenk tube, iron complex B (3.5 mg, 0.005 mmol) was admitted as catalyst and dissolved in dimethoxyethane (2 mL). To the solution, 1-octene (112 mg, 1.0 mmol) was added. The solution was transferred into an autoclave, whose interior was purged with hydrogen. In a hydrogen atmosphere of 10 atm., the solution was stirred at 80° C. for 30 minutes. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 3 in Table 2.

TABLE 2

| Entry | Cat | Cat loading (x) (mol %) | H$_2$ (atm) | Time (h) | Yield (%) |
|---|---|---|---|---|---|
| 1 | A | 0.5 | 1 | 2 | >99 |
| 2 | A | 0.05 | 20 | 6 | >99 |
| 3 | B | 0.5 | 10 | 0.5 | >99 |

(4) Hydrogenation of Styrene Using Iron Complex

[Chemical Formula 18]

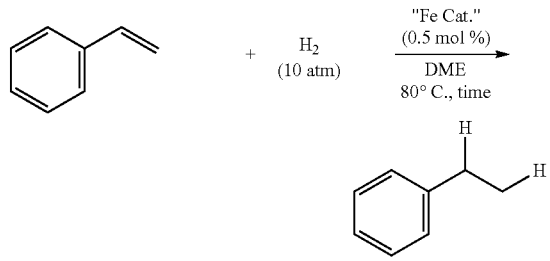

[Example 10] Hydrogenation of Styrene Using Iron Complex A

A 20-mL Schlenk tube equipped with a magnetic stirrer was heat dried while pumping to a vacuum of 5 Pa before its interior was purged with argon atmosphere. Into the Schlenk tube, iron complex A (3.7 mg, 0.005 mmol) was admitted as catalyst and dissolved in dimethoxyethane (2 mL). To the solution, styrene (114 μL, 1.0 mmol) was added. The solution was transferred into an autoclave, whose interior was purged with hydrogen. In a hydrogen atmosphere of 10 atm., the solution was stirred at 80° C. for 10 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 1 in Table 3.

$^1$H-NMR (CDCl$_3$, 400 MHz)
δ=1.13 (t, $J_{HH}$=7.2 Hz, 3H, CH$_2$CH$_3$), 2.54 (q, $J_{HH}$=7.2 Hz, 2H, CH$_2$CH$_3$), 7.02-7.11 (m, 3H, C$_6$H$_5$), 7.11-7.20 (m, 2H, C$_6$H$_5$)

$^{13}$C-NMR (100 MHz, CDCl$_3$)
δ=15.6, 28.8, 125.6, 127.8, 128.3, 144.3

[Example 11] Hydrogenation of Styrene Using Iron Complex B

A 20-mL Schlenk tube equipped with a magnetic stirrer was heat dried while pumping to a vacuum of 5 Pa before its interior was purged with argon atmosphere. Into the Schlenk tube, iron complex B (3.5 mg, 0.005 mmol) was admitted as catalyst and dissolved in dimethoxyethane (2 mL). To the solution, styrene (114 μL, 1.0 mmol) was added. The solution was transferred into an autoclave, whose interior was purged with hydrogen. In a hydrogen atmosphere of 10 atm., the solution was stirred at 80° C. for 10 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 2 in Table 3.

[Example 12] Hydrogenation of Styrene Using Iron Complex C

A 20-mL Schlenk tube equipped with a magnetic stirrer was heat dried while pumping to a vacuum of 5 Pa before its interior was purged with argon atmosphere. Into the Schlenk tube, iron complex C (3.8 mg, 0.005 mmol) was admitted as catalyst and dissolved in dimethoxyethane (2 mL). To the solution, styrene (114 μL, 1.0 mmol) was added. The solution was transferred into an autoclave, whose interior was purged with hydrogen. In a hydrogen atmosphere of 10 atm., the solution was stirred at 80° C. for 24 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 3 in Table 3.

TABLE 3

| Entry | Cat | Cat loading (x) (mol %) | Time (h) | Yield (%) |
|---|---|---|---|---|
| 1 | A | 0.5 | 10 | >99 |
| 2 | B | 0.5 | 10 | >99 |
| 3 | C | 0.5 | 24 | 77 |

(5) Hydrogenation of Olefin Using Iron Complex A

[Chemical Formula 19]

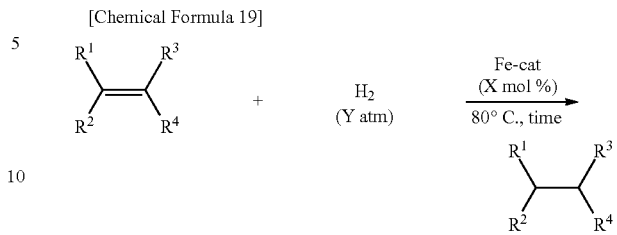

[Example 13] Hydrogenation of Methyl 10-undecenoate

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in dimethoxyethane (2 mL). To the solution, methyl 10-undecenoate (198 mg, 1.0 mmol) was added. The solution was transferred into an autoclave, whose interior was purged with hydrogen. In a hydrogen atmosphere of 10 atm., the solution was stirred at 80° C. for 2 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 1 in Table 4.

$^1$H-NMR (CDCl$_3$, 400 MHz)
δ=0.88 (t, 3H, $J_{H-H}$=7.4 Hz, —CH$_3$), 1.17-1.35 (m, 14H, —CH$_2$—), 1.53-1.67 (m, 2H, —CH$_2$—), 2.30 (t, 2H, $J_{H-H}$=7.7 Hz, —CH$_2$C(=O)—), 3.66 (s, 3H, OMe)

$^{13}$C-NMR (100 MHz, CDCl$_3$)
δ=14.25, 22.83, 25.12, 29.31, 29.40, 29.45, 29.60, 29.70, 32.04, 34.28, 51.57, 174.50

[Example 14] Hydrogenation of Trans-Stilbene

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in dimethoxyethane (2 mL). To the solution, trans-stilbene (180 mg, 1.0 mmol) was added. The solution was transferred into an autoclave, whose interior was purged with hydrogen. In a hydrogen atmosphere of 10 atm., the solution was stirred at 80° C. for 2 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 2 in Table 4.

$^1$H-NMR (CDCl$_3$, 400 MHz)
δ=2.93 (s, 4H, CH$_2$), 7.12-7.23 (m, 6H, C$_6$H$_5$), 7.24-7.32 (m, 4H, C$_6$H$_5$)

$^{13}$C-NMR (CDCl$_3$, 100 MHz)
δ=37.9, 125.9, 128.3, 128.5, 141.8

[Example 15] Hydrogenation of Cyclopentene

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in dimethoxyethane (2 mL). To the solution, cyclopentene (88.4 μL, 1.0 mmol) was added. The solution was transferred into an autoclave, whose interior was purged with hydrogen. In a hydrogen atmosphere of 10 atm., the solution was stirred at 80° C. for 2 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 3 in Table 4.

$^1$H-NMR (CDCl$_3$, 400 MHz) δ=1.52 (s, 10H, CH$_2$)
$^{13}$C-NMR (CDCl$_3$, 100 MHz) δ=25.9

[Example 16] Hydrogenation of 1-methyl-1-cyclohexene

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in dimethoxyethane (2 mL). To the solution, 1-methyl-1-cyclohexene (118 μL, 1.0 mmol) was added. The solution was transferred into an autoclave, whose interior was purged with hydrogen. In a hydrogen atmosphere of 10 atm., the solution was stirred at 80° C. for 2 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 4 in Table 4.

$^1$H-NMR (CDCl$_3$, 400 MHz)
δ=0.86 (d, J$_{HH}$=5.8 Hz, 3H, CH$_3$), 1.04-1.28 (m, 4H, CH$_2$), 1.28-1.39 (m, 1H, CH), 1.54-1.72 (m, 6H, CH$_2$)
$^{13}$C-NMR (CDCl$_3$, 100 MHz)
δ=22.9, 26.3, 26.4, 32.7, 35.4

[Example 17] Hydrogenation of ethyl 2,3-dimethylacrylate

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in dimethoxyethane (2 mL). To the solution, ethyl 2,3-dimethylacrylate (128 mg, 1.0 mmol) was added. The solution was transferred into an autoclave, whose interior was purged with hydrogen. In a hydrogen atmosphere of 10 atm., the solution was stirred at 80° C. for 2 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 5 in Table 4.

$^1$H-NMR (CDCl$_3$, 400 MHz)
δ=0.93-0.96 (m, 6H, Me), 1.28 (t, 3H, OCH$_2$C$\underline{H}_3$), 2.00-2.04 (m, 1H, CH and CH$_2$C(=O)), 4.19 (q, 2H, OC$\underline{H}_2$CH$_3$)
$^{13}$C-NMR (CDCl$_3$, 100 MHz)
δ=14.6, 22.9, 26.0, 43.6, 60.3, 173.5

[Example 18] Hydrogenation of (±)-limonene

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in dimethoxyethane (2 mL). To the solution, (±)-limonene (136 mg, 1.0 mmol) was added. The solution was transferred into an autoclave, whose interior was purged with hydrogen. In a hydrogen atmosphere of 10 atm., the solution was stirred at 80° C. for 10 hours. With anisole (108 mg, 1.0 mmol) added as internal standard, the geometry and yield of the product were determined by $^1$H-NMR spectroscopy. The resulting compound was identified for geometry (trans:cis=1:1) by $^1$H and $^{13}$C-NMR spectroscopy. The results are shown as Entry 6 in Table 4.

$^1$H-NMR (CDCl$_3$, 400 MHz)
δ=0.847 (d, 2H, J$_{HH}$=6.8 Hz, CH(CH$_3$)$_2$ of trans-isomer), 0.859 (d, 3H, J$_{HH}$=6.8 Hz, CH$_3$ of trans-isomer), 0.860 (d, 2H, J$_{HH}$=6.8 Hz, CH(CH$_3$)$_2$ of cis-isomer), 0.909 (d, 3H, J$_{HH}$=6.8 Hz, CH$_3$ of cis-isomer), 0.87-1.09 (m, 2H, CH and CH$_2$), 1.18-1.58 (m, 6H, CH and CH$_2$), 1.62-1.77 (m, 3H, CH$_2$)
$^{13}$C-NMR (CDCl$_3$, 100 MHz)
δ=19.5, 20.0, 20.4, 22.9, 25.5, 29.3, 29.7, 31.6, 33.0, 33.1, 35.8, 43.2, 44.0

[Example 19] Hydrogenation of α-methylstilbene

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in DME (2 mL). To the solution, α-methylstilbene (194 mg, 1.0 mmol) was added. The solution was transferred into an autoclave, whose interior was purged with hydrogen. In a hydrogen atmosphere of 10 atm., the solution was stirred at 80° C. for 10 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 7 in Table 4.

$^1$H-NMR (CDCl$_3$, 400 MHz)
δ=1.30 (d, 3H, J$_{HH}$=6.8 Hz, CH$_3$), 2.78-2.91 (m, 1H, CH(Me)), 2.98-3.08 (m, 1H, CH$_2$Ph), 7.12-7.40 (m, 10H, Ph)
$^{13}$C-NMR (CDCl$_3$, 100 MHz)
δ=21.2, 42.0, 45.1, 125.9, 126.1, 127.0, 128.1, 128.3, 129.4, 141.0, 147.2

[Example 20] Hydrogenation of 2,3-dimethyl-2-butene

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in dimethoxyethane (2 mL). To the solution, 2,3-dimethyl-2-butene (84 mg, 1.0 mmol) was added. The solution was transferred into an autoclave, whose interior was purged with hydrogen. In a hydrogen atmosphere of 10 atm., the solution was stirred at 80° C. for 6 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 8 in Table 4.

$^1$H-NMR (CDCl$_3$, 400 MHz)
δ=0.84 (d, J$_{H-H}$=6.7 Hz, 12H, CH$_3$), 1.40 (septet, J$_{H-H}$=6.7 Hz, 12H, CH)
$^{13}$C-NMR (CDCl$_3$, 100 MHz)
δ=19.4, 33.7

[Example 21] Hydrogenation of 2,3-dimethyl-1H-indene

A 20-mL Schlenk tube equipped with a magnetic stirrer was heat dried while pumping to a vacuum of 5 Pa before its interior was purged with argon atmosphere. Into the Schlenk tube, iron complex A (7.3 mg, 0.01 mmol) was admitted as catalyst and dissolved in DME (2 mL). To the solution, 2,3-dimethyl-1H-indene (144 mg, 1.0 mmol) was added. The solution was transferred into an autoclave, whose interior was purged with hydrogen. In a hydrogen atmosphere of 20 atm., the solution was stirred at 80° C. for 10 hours. With anisole (108 mg, 1.0 mmol) added as internal standard, the geometry and yield of the product were determined by $^1$H-NMR spectroscopy. The resulting compound was identified for geometry by $^1$H and $^{13}$C-NMR spectroscopy. The results are shown as Entry 9 in Table 4.

$^1$H-NMR (CDCl$_3$, 400 MHz)

δ=0.94 (d, 3H, J=6.9 Hz, CH$_3$CHCH$_2$), 1.14 (d, 3H, J=7.2 Hz, CH$_3$CH), 2.49-2.61 (m, 2H), 2.94 (m, 1H), 3.17 (quintet, 1H, J=6.9 Hz, CH$_3$CH), 7.06-7.24 (m, 4H, C$_6$H$_4$)

$^{13}$C-NMR (CDCl$_3$, 100 MHz)

δ=14.5, 15.0, 37.8, 39.2, 42.6, 123.5, 124.3, 126.0, 126.1, 142.8, 149.0

TABLE 4

| Entry | Alkene | Cat loading (x) (mol %) | H$_2$ (atm) | Time (h) | Yield (%) |
|---|---|---|---|---|---|
| 1 | (9-decenoic acid methyl ester) | 1 | 10 | 2 | >99 |
| 2 | (stilbene) | 1 | 10 | 2 | >99 |
| 3 | (cyclopentene) | 1 | 10 | 2 | >99 |
| 4 | (1-methylcyclohexene) | 1 | 10 | 2 | >99 |
| 5 | (ethyl 3,3-dimethylacrylate) | 1 | 10 | 2 | >99 |
| 6 | (limonene) | 1 | 10 | 10 | 50 |
| 7 | (α-methylstilbene) | 1 | 10 | 10 | >99 |
| 8 | (2,3-dimethyl-2-butene) | 1 | 10 | 6 | >99 |
| 9 | (2,3-dimethyl-1H-indene) | 1 | 20 | 10 | >99 |

(6) Reduction of Amide Using Iron Complex

[Chemical Formula 20]

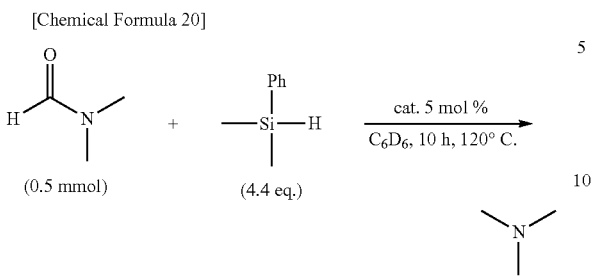

[Example 22] Reduction of N,N-dimethylformamide Using Iron Complex A

A NMR tube was heat dried while pumping to a vacuum of 5 Pa. Into the tube, iron complex A (18 mg, 0.025 mmol) was admitted as catalyst, and heavy benzene (0.4 mL) was added through a syringe. Thereafter, dimethylphenylsilane (30 mg, 0.22 mmol) was added, and N,N-dimethylformamide (36.5 mg, 0.5 mmol) added, after which the NMR tube was burnt off under reduced pressure for vacuum sealing. The solution was stirred at 120° C. for 10 hours. The formation of amine was confirmed by $^1$H-NMR spectroscopy. The results are shown as Entry 1 in Table 5.

$^1$H-NMR (CDCl$_3$, 400 MHz) δ=2.12 (s, 9H, NMe$_3$)

[Example 23] Reduction of N,N-dimethylformamide Using Iron Complex B

A NMR tube was heat dried while pumping to a vacuum of 5 Pa. Into the tube, iron complex B (18 mg, 0.025 mmol) was admitted as catalyst, and heavy benzene (0.4 mL) was added through a syringe. Thereafter, dimethylphenylsilane (30 mg, 0.22 mmol) was added, and N,N-dimethylformamide (36.5 mg, 0.5 mmol) added, after which the NMR tube was burnt off under reduced pressure for vacuum sealing. The solution was stirred at 120° C. for 10 hours. The formation of amine was confirmed by $^1$H-NMR spectroscopy. The results are shown as Entry 2 in Table 5.

TABLE 5

| Entry | Cat | Cat loading (x) (mol %) | Yield (%) |
|---|---|---|---|
| 1 | A | 5 | >99 |
| 2 | B | 5 | >99 |

(7) Reductive Reaction of Aldehyde Using Iron Complex B

[Example 24] Reduction of 4-methoxybenzaldehyde

A NMR tube was heat dried while pumping to a vacuum of 5 Pa. Into the tube, iron complex B (18 mg, 0.025 mmol) was admitted as catalyst, and heavy benzene (0.4 mL) was added through a syringe. Thereafter, 1,1,3,3-tetramethyldisiloxane (101 mg, 0.75 mmol), 4-methoxybenzaldehyde (68 mg, 0.5 mmol), and hexamethylbenzene (32.4 mg, 0.05 mmol) as internal standard were added, after which the NMR tube was burnt off under reduced pressure for vacuum sealing. The solution was stirred at 60° C. for 10 hours. The formation of alcohol silyl ether was confirmed by $^1$H-NMR spectroscopy (yield 94%). The resulting alcohol silyl ether was identified for geometry by $^1$H and $^{13}$C-NMR spectroscopy.

$^1$H-NMR (CDCl$_3$, 400 MHz)
δ=0.12 (s, 6H, SiMe$_2$), 0.18 (d, 6H, J$_{Si-H}$=3.9 Hz, Si(H)Me$_2$), 3.79 (s, 3H, OMe), 4.70 (s, 2H, CH$_2$), 4.73 (sept, 1H, J$_{Si-H}$=3.9 Hz, SiH), 6.86-6.89 (m, 2H, C$_6$H$_4$), 7.20-7.23 (m, 2H, C$_6$H$_4$)

$^{13}$C-NMR (CDCl$_3$, 99.5 MHz)
δ=−0.99, 0.74, 55.21, 64.01, 113.76, 128.20, 132.91, 158.95

The invention claimed is:

1. A mononuclear iron bivalent complex having formula (1):

[Chemical Formula 1]

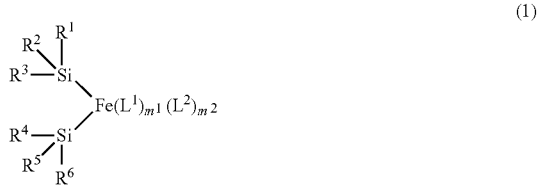

(1)

wherein R$^1$ to R$^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl or organothio group which may be substituted with X, or at least one pair of any one of R$^1$ to R$^3$ and any one of R$^4$ to R$^6$, taken together, represent a crosslinking substituent, X is a halogen atom, organoxy, monoorganoamino, diorganoamino or organothio group, L$^1$ is a two-electron ligand being isonitrile, with the proviso that when a plurality of L$^1$'s are present, two L$^1$'s may bond together, L$^2$ is a two-electron ligand other than CO ligand and L$^1$, with the proviso that when a plurality of L$^2$'s are present, two L$^2$'s may bond together, m$^1$ is an integer of 1 to 4, m$^2$ is an integer of 0 to 3, and m$^1$+m$^2$ is 3 or 4.

2. The mononuclear iron bivalent complex of claim 1 wherein L$^2$ is triorganohydrosilane, with the proviso that when a plurality of L$^2$'s are present, two L$^2$'s may bond together.

3. The mononuclear iron bivalent complex of claim 1 wherein m$^1$ and m$^2$ each are 2.

4. The mononuclear iron bivalent complex of claim 3 wherein R$^1$ to R$^6$ are each independently an alkyl, aryl or aralkyl group which may be substituted with X which is as defined above, L$^2$ is a triorganohydrosilane represented by H—SiR$^7$R$^8$R$^9$ or H—SiR$^{10}$R$^{11}$R$^{12}$ wherein R$^7$ to R$^{12}$ are each independently an alkyl, aryl or aralkyl group which may be substituted with X which is as defined above, at least one pair of any one of R$^1$ to R$^3$ and any one of R$^4$ to R$^6$ or any one of R$^7$ to R$^9$, or at least one pair of any one of R$^{10}$ to R$^{12}$ and any one of R$^4$ to R$^6$ or any one of R$^7$ to R$^9$ may bond together to form a crosslinking substituent, or at least one pair of any one of R$^1$ to R$^3$ and any one of R$^4$ to R$^6$ or any one of R$^7$ to R$^9$ may bond together to form a crosslinking substituent, and at least one pair of any one of $R^{10}$ to $R^{12}$ and any one of $R^4$ to $R^6$ or any one of $R^7$ to $R^9$ may bond together to form a crosslinking substituent.

5. The mononuclear iron bivalent complex of claim 4 wherein any one of $R^1$ to $R^3$ and any one of $R^4$ to $R^6$ or any one of $R^7$ to $R^9$ bond together to form a crosslinking substituent, and any one of $R^{10}$ to $R^{12}$ and a substituent on Si which is selected from any one of $R^4$ to $R^6$ and any one of $R^7$ to $R^9$ and which does not participate in formation of said crosslinking substituent bond together to form a crosslinking substituent.

6. The mononuclear iron bivalent complex of claim 5 wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and any one of $R^{10}$ to $R^{12}$ and any one of $R^7$ to $R^9$ bond together to form an o-phenylene group which may be substituted with Y which is as defined above.

7. The mononuclear iron bivalent complex of claim 1 wherein any one of $R^1$ to $R^3$ and any one of $R^4$ to $R^6$ bond together to form a crosslinking substituent.

8. A mononuclear iron bivalent complex having formula (1):

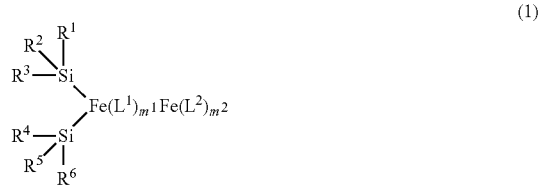

(1)

wherein $R^1$ to $R^6$ are each independently an alkyl, aryl or aralkyl group which may be substituted with X, X is a halogen atom, organoxy, monoorganoamino, diorganoamino or organothio group, $L^1$ is at least one two-electron ligand selected from the group consisting of isonitrile, amine, imine, nitrogen-containing heterocyclic ring, phosphine, phosphite, and sulfide, with the proviso that when a plurality of $L^1$'s are present, two $L^1$'s may bond together, $L^2$ is a triorganohydrosilane represented by H—$SiR^7R^8R^9$ or H—$SiR^{10}R^{11}R^{12}$ wherein $R^7$ to $R^{12}$ are each independently an alkyl, aryl or aralkyl group which may be substituted with X which is as defined above with the proviso that when a plurality of $L^2$'s are present, two $L^2$'s may bond together, any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and any one of $R^{10}$ to $R^{12}$ and any one of $R^7$ to $R^9$ bond together to form an o-phenylene group which may be substituted with Y which is as defined above, $m^1$ and $m^2$ each are 2.

9. A catalyst comprising the mononuclear iron bivalent complex of claim 1 or 8, the catalyst having activity to at least one reaction selected from hydrosilylation reaction, hydrogenation reaction, and reductive reaction of carbonyl compounds.

10. A method for preparing an addition compound, comprising the step of effecting hydrosilylation reaction of a compound having an aliphatic unsaturated bond with a hydrosilane or organohydropolysiloxane having a Si—H bond in the presence of the catalyst of claim 9.

11. A method for preparing an alkane compound, comprising the step of hydrogenating a compound having an aliphatic unsaturated bond in the presence of the catalyst of claim 9.

12. A method for preparing an amine compound, comprising the step of reducing an amide compound with a silane or organohydropolysiloxane having a Si—H bond in the presence of the catalyst of claim 9.

13. A method for preparing an alcohol compound, comprising the step of reducing an aldehyde, ketone or ester compound with a silane or organohydropolysiloxane having a Si—H bond in the presence of the catalyst of claim 9.

* * * * *